US008292801B2

(12) United States Patent
Dejima et al.

(10) Patent No.: US 8,292,801 B2
(45) Date of Patent: Oct. 23, 2012

(54) SURGICAL TREATMENT APPARATUS

(75) Inventors: Takumi Dejima, Tokyo (JP); Ryo Minosawa, Tsukui-gun (JP); Takahiro Kogasaka, Tokyo (JP)

(73) Assignee: Olympus Medical Systems Corp. (JP)

( * ) Notice: Subject to any disclaimer, the term of this patent is extended or adjusted under 35 U.S.C. 154(b) by 1505 days.

(21) Appl. No.: 11/615,469

(22) Filed: Dec. 22, 2006

(65) Prior Publication Data

US 2008/0154091 A1 Jun. 26, 2008

(51) Int. Cl.
*A61B 1/00* (2006.01)
(52) U.S. Cl. ........................................ 600/104
(58) Field of Classification Search .................. 600/104, 600/106, 114, 117, 137
See application file for complete search history.

(56) References Cited

U.S. PATENT DOCUMENTS

| | | | | | |
|---|---|---|---|---|---|
| 4,607,619 | A | * | 8/1986 | Seike et al. | 600/106 |
| 4,852,550 | A | * | 8/1989 | Koller et al. | 600/106 |
| 5,381,784 | A | * | 1/1995 | Adair | 600/166 |
| 5,538,497 | A | * | 7/1996 | Hori | 600/182 |
| 5,954,731 | A | * | 9/1999 | Yoon | 606/144 |
| 6,277,064 | B1 | * | 8/2001 | Yoon | 600/114 |
| 2002/0099263 | A1 | * | 7/2002 | Hale et al. | 600/117 |
| 2002/0103420 | A1 | * | 8/2002 | Coleman et al. | 600/173 |
| 2002/0143319 | A1 | * | 10/2002 | Brock | 606/1 |
| 2003/0114730 | A1 | * | 6/2003 | Hale et al. | 600/114 |
| 2003/0120130 | A1 | * | 6/2003 | Glukhovsky et al. | 600/109 |
| 2004/0138525 | A1 | * | 7/2004 | Saadat et al. | 600/104 |
| 2005/0004431 | A1 | * | 1/2005 | Kogasaka et al. | 600/117 |
| 2005/0027167 | A1 | * | 2/2005 | Chatenever et al. | 600/173 |
| 2005/0154260 | A1 | * | 7/2005 | Schara et al. | 600/117 |
| 2005/0234296 | A1 | * | 10/2005 | Saadat et al. | 600/129 |
| 2006/0149129 | A1 | * | 7/2006 | Watts et al. | 600/113 |
| 2007/0106113 | A1 | * | 5/2007 | Ravo | 600/113 |

FOREIGN PATENT DOCUMENTS

DE 4324254 C1 * 1/1995
JP 2001-212078 8/2001

OTHER PUBLICATIONS

Japanese Office Action mailed Jun. 20, 2012 in connection with corresponding Japanese Patent Application No. 2007-328987.
English translation of Japanese Office Action issued in connection with corresponding Japanese application provided as an explanation of prior art relevancy.

* cited by examiner

*Primary Examiner* — Philip R Smith
*Assistant Examiner* — William Chou
(74) *Attorney, Agent, or Firm* — Ostrolenk Faber LLP

(57) ABSTRACT

A surgical treatment apparatus according to the present invention includes an outer sheath, extending from a base portion subject to an operator's hand to the tip subject to insertion into a body cavity, that is provided with a working channel through which a treatment instrument can be passed; an image pickup device disposed at the tip portion of the outer sheath; and pivotable forceps disposed at the tip portion of the outer sheath, supported on a supporting section protruding in the axial direction via a joint being bent away from the working channel, and having a pair of forceps members arranged so as to be freely opened/closed, wherein the image pickup device is disposed at a position between the axis line of the supporting section and the axis line of the working channel and offset from an imaginary line connecting the two axis lines.

3 Claims, 26 Drawing Sheets

SURGICAL TREATMENT APPARATUS

BACKGROUND OF THE INVENTION

1. Field of the Invention

The present invention relates to an apparatus for carrying out surgical treatment.

2. Background Art

When a medical practice, such as observation or treatment, is carried out on human organs and the like, treatment instruments, such as an endoscope and forceps, are occasionally inserted through a natural opening in a living body. When a medical practice is carried out in an abdominal cavity, a plurality of openings are formed in the abdominal wall, instead of making a large incision in the abdominal wall. Treatment instruments, such as an endoscope and forceps, are inserted, one for each opening, in some cases. Since this is made possible only by forming small openings in the abdominal wall, it is advantageous that invasion into the patient is minimal and that the patient can recuperate rapidly.

For example, when a tumor has developed in the bladder, forceps are transurethrally inserted into the bladder to remove the tumor. Furthermore, in the case of removing a tumor developed in the mediastinum, a plurality of openings are formed so as to avoid the ribs, forceps and an endoscope are inserted through the openings, one for each opening, and treatment is carried out while the endoscope is used to observe the forceps that have been inserted at a different angle to approach the tumor. The positions and angles at which the forceps and the endoscope are inserted are limited in order to avoid the ribs. In addition, the forceps and the endoscope are required to approach the area to be treated while the forceps and endoscope are tilted at some angles. For this reason, the operation is difficult. When the endoscope is used to perform observation during treatment or to check for any remaining tumor after the treatment, the treatment area is obstructed by the ribs and cannot be viewed in some cases. When transurethral manipulation is used, it is difficult to perform observation while carrying out treatment because the inlet of the opening is narrow and there is no space for forming a plurality of openings. For these reasons, forceps being configured so that their tips are bent inside the body and endoscopes that can be bent inside the body have been conventionally developed.

SUMMARY OF THE INVENTION

In one aspect of the present invention, a surgical treatment apparatus includes an outer sheath, extending from a base portion subject to an operator's hand to the tip subject to insertion into a body cavity, that is provided with a working channel through which a treatment instrument can be passed; an image pickup device disposed at the tip portion of the outer sheath; and pivotable forceps disposed at the tip portion of the outer sheath, supported on a supporting section protruding in the axial direction via a joint being bent away from the working channel, and having a pair of forceps members arranged so as to be freely opened/closed. The image pickup device is disposed at a position between the axis line of the supporting section and the axis line of the working channel and offset from an imaginary line connecting the two axis lines.

In another aspect of the present invention, the surgical treatment apparatus includes an outer sheath, extending from a base portion subject to an operator's hand to the tip subject to insertion into a body cavity, that is provided with a working channel through which a treatment instrument can be passed; an image pickup device disposed at the tip portion of the outer sheath and being movable to a position offset from the axis line of the outer sheath; pivotable forceps passed through the outer sheath so as to freely extend/retract and provided with a pair of forceps members arranged so as to be freely opened/closed and freely bent upward in a direction substantially orthogonal to the opening/closing direction thereof; and a treatment instrument arranged so as to be freely protruded from and sunk into an opening formed in the sheath of the pivotable forceps and used to treat tissue inside the body when the pair of forceps members are bent upward.

DETAILED DESCRIPTION OF THE INVENTION

The embodiments will be described below. In the embodiments, the same contents are designated by the same numerals. In addition, overlapping descriptions between the embodiments will be omitted.

First Embodiment

Figure 1:
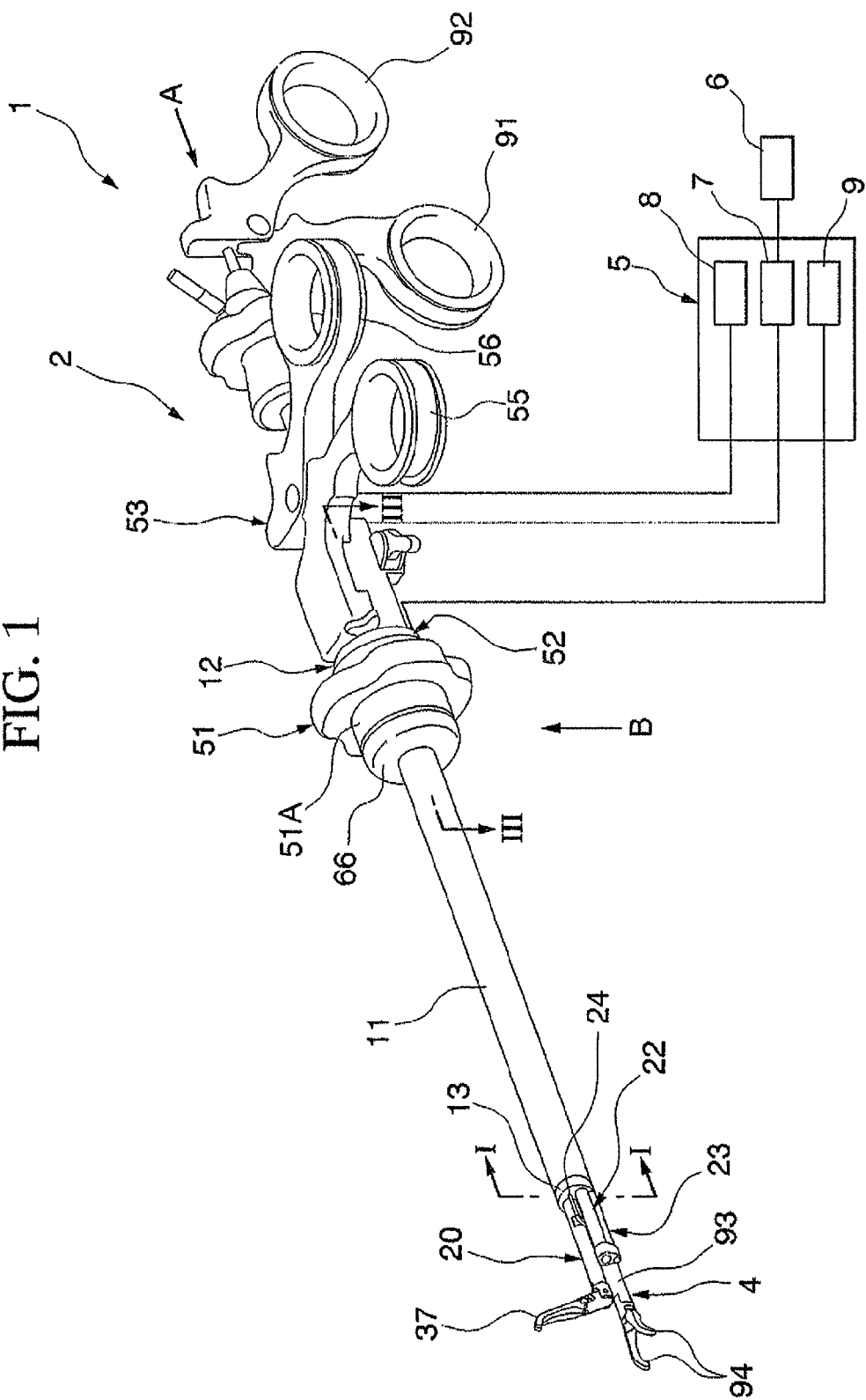
FIG. 1 is a view showing the configuration of a surgical treatment apparatus.

As shown in FIG. 1 in a surgical treatment apparatus 1, a long, thin and hard insertion section 3 extends from an operation section 2 that is operated outside the body by the operator, and forceps 4 serving as a replaceable treatment instrument are inserted into the insertion section 3. Furthermore, the surgical treatment apparatus 1 is connected to a control unit 5, whereby it is possible to carry out image processing and display on a monitor 6 as described later. Although the forceps 4 are shown in FIG. 1 as a treatment instrument, a clip or the like may also be used.

Figure 2:
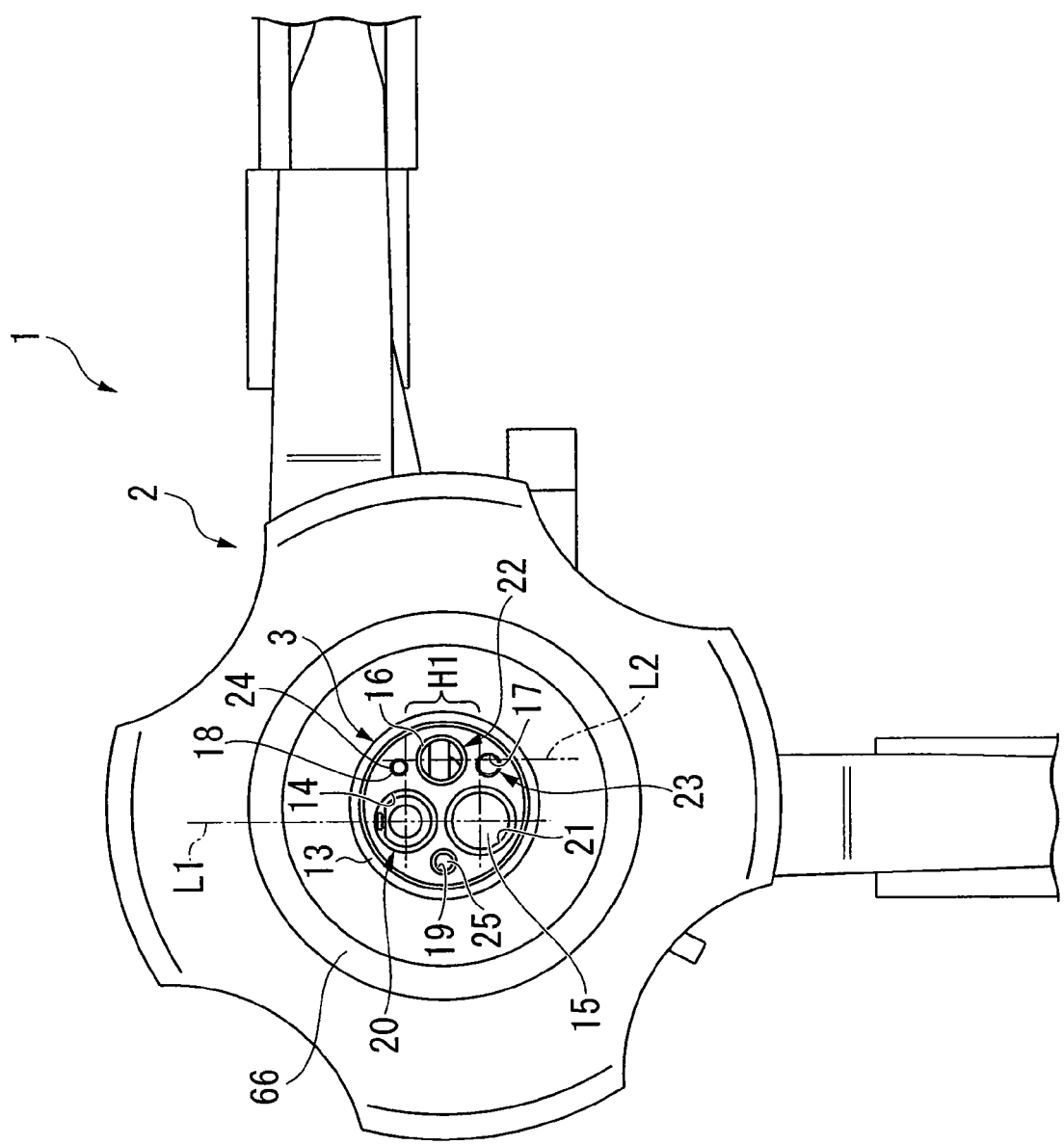
FIG. 2 is a sectional view taken along line I-I in FIG. 1.

The insertion section 3 has a cylindrical outer sheath 11. An end cap 12 is fitted on the base portion on the hand side of the operator, and an end cap 13 is fitted on the tip portion that is inserted into the body. As shown in FIG. 1 and FIG. 2, six ducts 14, 15, 16, 17, 18 and 19 are formed in the end cap 13 parallel with the axial direction of the insertion section 3. Pivotable forceps 20 serving as a treatment instrument characteristic of the surgical treatment apparatus 1 is disposed in the duct 14. In the duct 15, a working channel 21 into which the forceps 4 are replaceably inserted is formed. The duct 16 is disposed on an imaginary line L2 that is parallel with an imaginary line L1 connecting the centers of the two ducts 14 and 15. The duct 16 is positioned on the imaginary line L2 in an area H1 ranging from the position corresponding to the center of the duct 14 to the position corresponding to the center of the duct 15. In the duct 16, an image pickup device 22 is passed through so as to freely extend/retract. The ducts 17 and 18 are disposed near the duct 16. The light guide 23 of a lighting device is passed through the duct 17 so as to freely extend/retract. A wiper 24 for wiping the imaging area of the image pickup device 22 is passed through the duct 18 so as to freely rotate. The duct 19 is disposed on the opposite side of the duct 16 with respect to the imaginary line L1. A tube 25 for liquid supply, air supply and air suction is passed through the duct 19.

Figure 3:
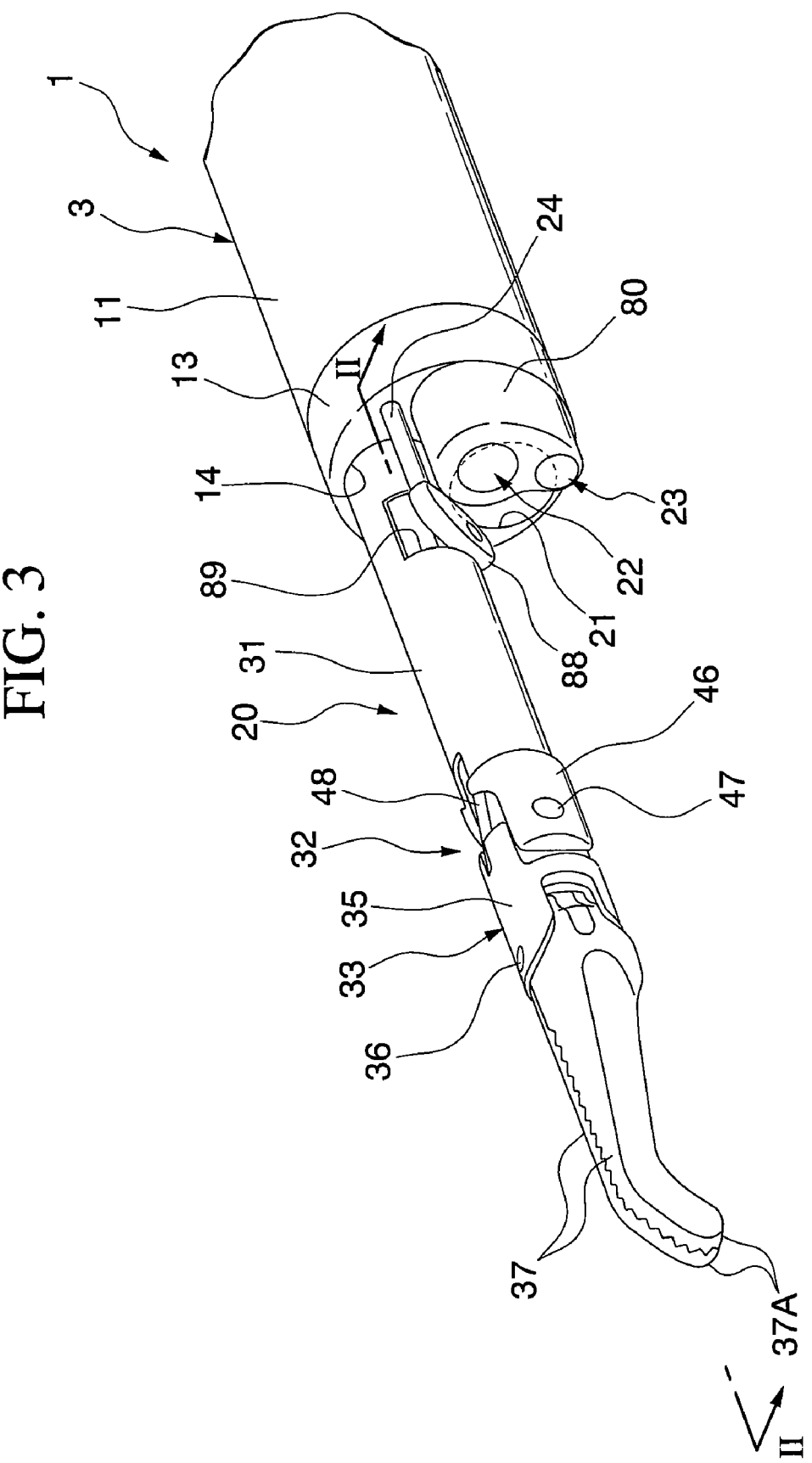
FIG. 3 is a perspective view showing the tip portion of the surgical treatment apparatus.

As shown in FIG. 3, in the pivotable forceps 20, a supporting tube 31 serving as a supporting section is passed through the insertion section 3. The tip portion of the supporting tube 31 protrudes from the end cap 13. The supporting tube 31 is disposed so as to freely rotate around the axis line of the supporting tube 31 itself within a predetermined angle with respect to the insertion section 3 but disposed so as not to be able to extend/retract with respect to the insertion section 3. Furthermore, at the tip portion of the supporting tube 31, a treatment section 33 is installed via a joint 32. The joint 32 has a mechanism that rotates the treatment section 33 to raise it on the opposite side of the working channel 21. The treatment section 33 is provided with a pair of forceps members 37 supported on a supporting member 35 via a pin 36 so as to freely open/close. The opening/closing direction of the forceps members 37 is substantially orthogonal to the direction in which the treatment section 33 rotates via the joint 32. The tip portions 37A of the forceps members 37 are bent toward the working channel 21.

Figure 4:
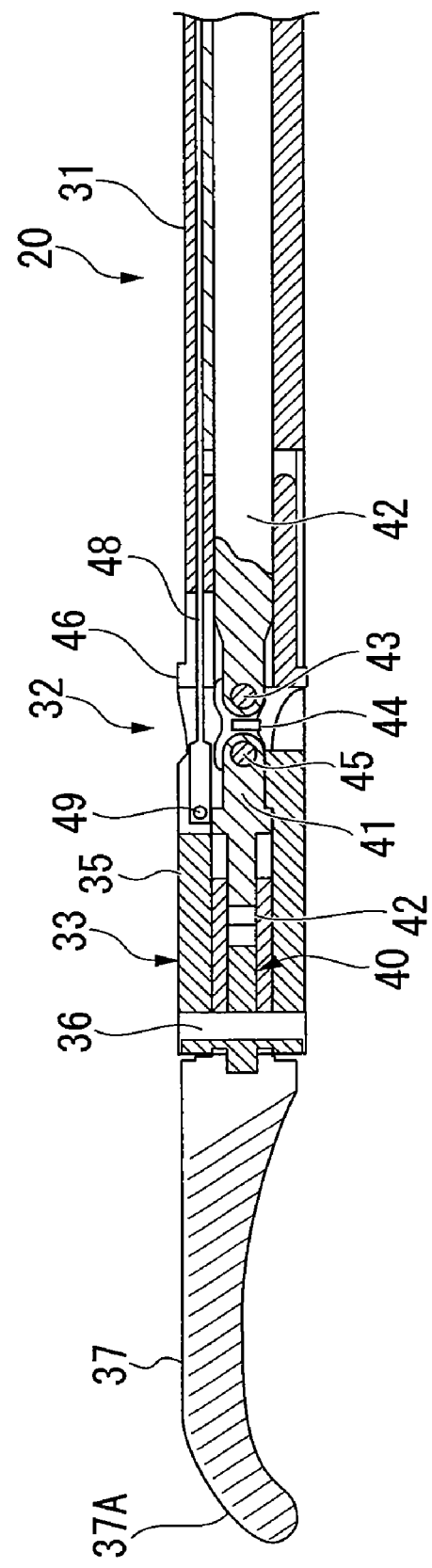
FIG. 4 is a sectional view taken along line II-II in FIG. 3.

As shown in FIG. 4, an opening/closing mechanism 40 for opening/closing the forceps members 37 is accommodated inside the supporting member 35. The opening/closing mechanism 40 is constituted of a link that converts the operation of a link rod 41 that extends/retracts in the axial direction into opening/closing operation. One end of the opening/closing mechanism 40 is connected to the base portions of the forceps members 37, and the other end thereof is connected to the link rod 41. The base portion of the link rod 41 is connected via the joint 32 to an opening/closing operation member 42 passed through the supporting tube 31. The joint 32 is configured so that the forceps members 37 can be opened/closed even when the treatment section 33 is bent with respect to the supporting tube 31. The joint 32 has a connection member 44 that is freely rotatably installed at the tip portion of the opening/closing operation member 42 via a pin 43. The connection member 44 extends from the base portion thereof pivotally supported using a pin 43 substantially along the longitudinal direction of the pivotable forceps 20. At the tip portion thereof, the link rod 41 is freely rotatably installed using a pin 45. Furthermore, a protection cover 46 is secured to the supporting tube 31 so as to enclose the connection member 44. As shown in FIG. 3, at the tip portion of the protection cover 46, the treatment section 33 is connected via a pin 47 so as to be freely bent.

A bending operation member 48 is passed through the supporting tube 31 so as to freely extend/retract and be offset from the center of the supporting tube 31. The tip portion of the bending operation member 48 passes the joint 32, enters the treatment section 33, and is secured to the base portion of the supporting member 35 by a pin 49. The tip portions of the protection cover 46 of the joint 32 and the supporting tube 31 are cut out so as to conform to the shape of the bending operation member 48. Hence, when the bending operation member 48 is pulled, the portion connected thereto via the pin 49 of the supporting member 35 is pulled, and the treatment section 33 can be rotated around the pin 47 and bent upward as shown in FIG. 1.

Figure 5:
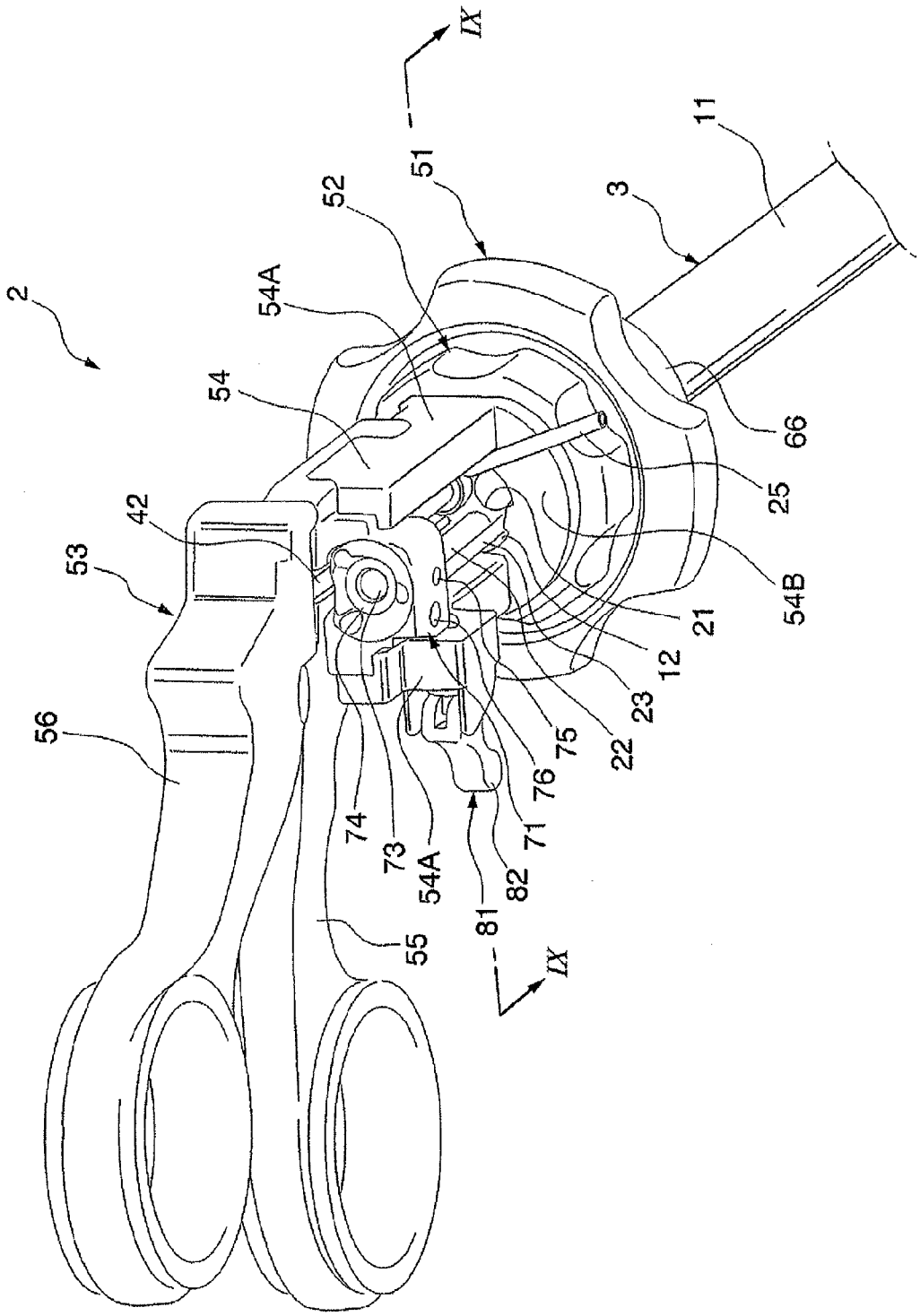
FIG. 5 is a view showing an operation section viewed from the direction A in FIG. 1.

As shown in FIG. 1 and FIG. 5, the operation section 2 of the surgical treatment apparatus 1 is supported on the end cap 12 of the insertion section 3 and is generally divided into a portion that is used to operate the pivotable forceps 20 and a portion that is used to operate the forceps 4.

The section that is used to operate the pivotable forceps 20 is mainly constituted of a first knob 51 serving as a first operation member for a bending operation, a second knob 52 serving as a second operation member for rotation operation, and an opening/closing operation section 53, in the order of installation from the side of the insertion section 3. The opening/closing operation section 53 has a pair of handles 55 and 56 mounted on the end cap 12 via a supporting section 54. The handle 55 is secured to the supporting section 54. The handle 56 freely opens/closes with respect to the handle 55 and is connected to the opening/closing operation member 42. When the handles 55 and 56 used as a pair are opened/closed, the opening/closing operation member 42 is extended/retracted.

When the pivotable forceps 20 are disposed in the surgical treatment apparatus 1 so as to be above the working channel 21, the pair of handles 55 and 56 are disposed on the right side, on the left side, or in the range from the right side through the lower side to the left side, as viewed from the operator. With this disposition, the operator can easily operate the opening/closing operation section 53. The opening/closing operation section 53 may also be configured so as to operate the opening/closing operation member 42 by extending/retracting a slider.

Figure 6:
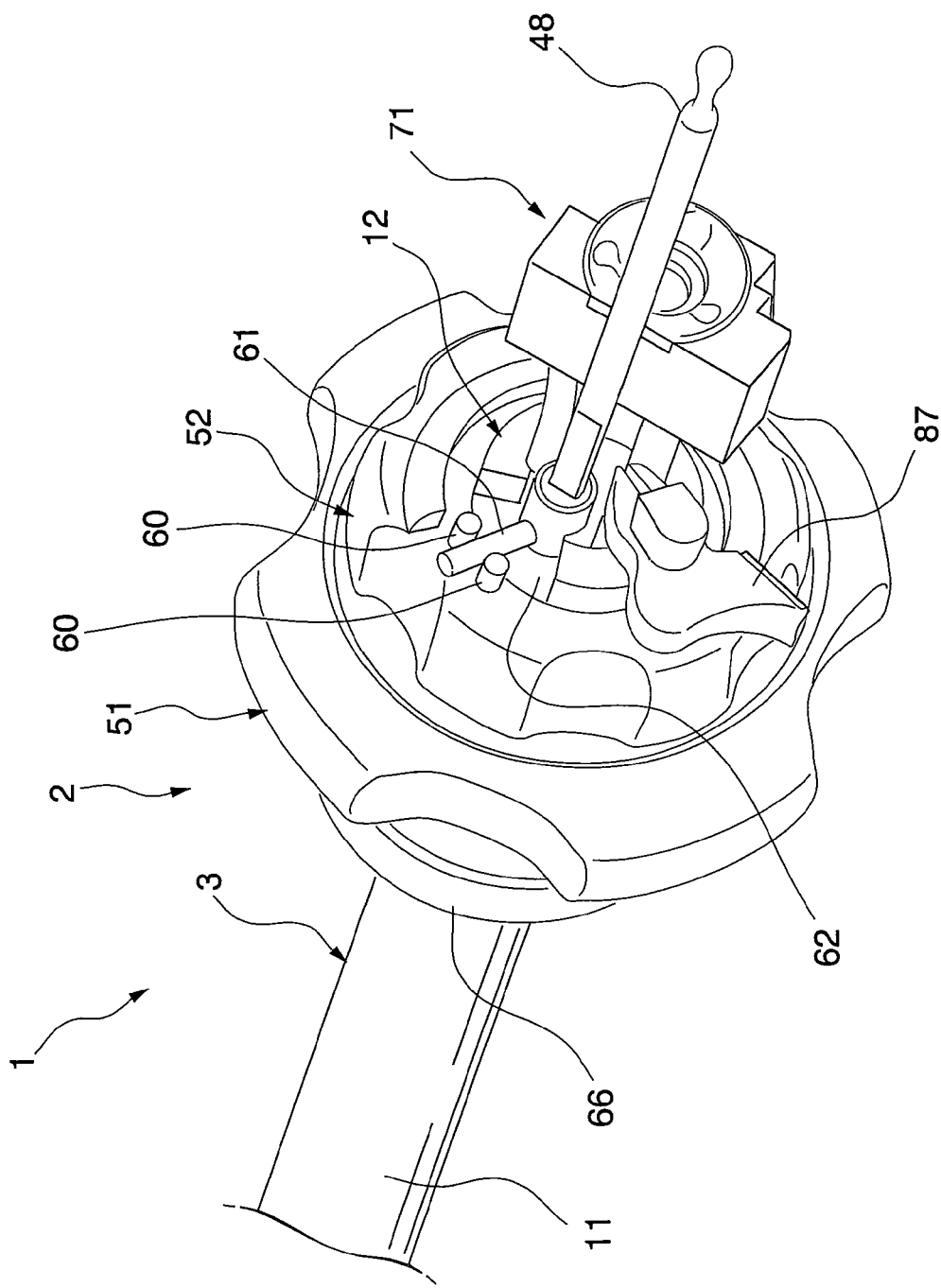
FIG. 6 is a partially exploded perspective view illustrating the configuration of the operation section.

The second knob 52 is freely rotatably mounted on the end cap 12. The rotation center of the second knob 52 is aligned with the axis line of the insertion section 3. As shown in FIG. 6, the second knob 52 is provided with a pair of pins 60 protruding toward the base portion in the axial direction. These pins 60 are secured in the circumferential direction with a predetermined clearance provided therebetween. A pin 61 is inserted between the pins 60. The pin 61 is secured to the supporting tube 31 of the pivotable forceps 20 and protrudes outward in the radial direction. With this configuration, when the second knob 52 is rotated, the pin 61 is engaged with the pins 60, and the supporting tube 31 is rotated in the rotation direction of the second knob 52. A notch is formed to the end cap 12 in a predetermined length in the circumferential direction so that the pin 61 is exposed. The recessing portion 62 formed of the notch is not moved even when the second knob 52 is rotated. Hence, the second knob 52 can rotate only a limited distance until the pin 61 makes contact with the step of the recessing portion 62. In other words, the recessing portion 62 serves as a restricting section that restricts the rotation angle of the supporting tube 31, that is, the rotation angle of the pivotable forceps 20. In this embodiment, the rotatable angle of the pivotable forceps 20 is ±45°. Although this angle is sufficient to facilitate treatment, the angle may have larger values.

Figure 7:
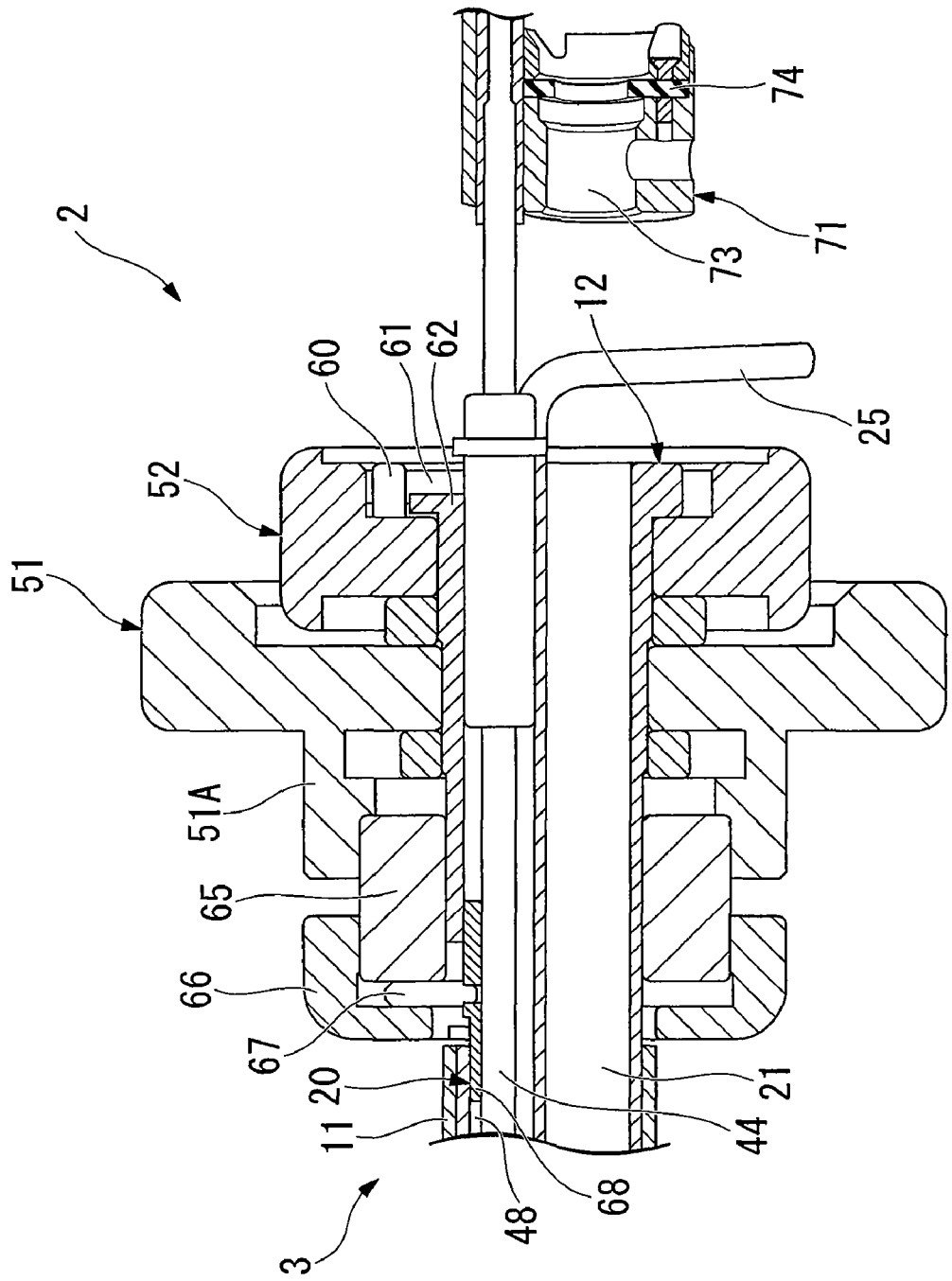
FIG. 7 is a sectional view taken along line III-III in FIG. 1.

As shown in FIG. 7, the first knob 51 is freely rotatably attached to the end cap 12, and its rotation center is aligned with the axis line of the insertion section 3. The tip portion 51A of the first knob 51 extends in a ring shape. A cylindrical moving piece 65 is threaded into the inner circumferential side of the tip portion 51A. A cover member 66 is secured to the outer circumference of the front end of the moving piece 65. A pin 67 is held between the moving piece 65 and the cover member 66. The pin 67 is pulled into the supporting tube 31 of the pivotable forceps 20 and connected to the base portion of the bending operation member 48 via a slider 68. With this configuration, when the first knob 51 is rotated, the moving piece 65 and the cover member 66 are extended/retracted in the axial direction while being rotated, and the pin 67 being held therebetween is moved. Hence, the bending operation member 48 connected to the pin 67 is extended/retracted, whereby bending is carried out. Since the first knob 51 is made larger than the second knob 52 in diameter, the knobs 51 and 52 can easily be distinguished from each other.

As shown in FIG. 5, the operation section 2 has, as sections for operating the forceps 4, the supporting section 54 secured to the end cap 12 and a mounting section 71 serving as an extending/retracting operation section that extends/retracts in the axial direction under the guidance of the supporting section 54. The supporting section 54 has a pair of guide portions 54A extending in the axial direction of the insertion section 3, and the mounting section 71 is held between the guide portions 54A. As shown in FIG. 5 and FIG. 7, a through hole 73 is formed in the mounting section 71 parallel with the axis line. The through hole 73 is provided at a position aligned with the working channel 21 as viewed in the axial direction and has a size into which the forceps 4 can be inserted. An elastic member 74 is secured inside the through hole 73. When the forceps 4 are inserted into the through hole 73, the elastic member 74 makes pressure contact with the forceps 4.

The image pickup device 22 and the light guide 23 of the lighting device are secured to the mounting section 71. The video cord of the image pickup device 22 and the light guide 23 are drawn out from holes 75 and 76 formed on the side of the mounting section 71 and connected to the control unit 5 (see FIG. 1). With this configuration, the image pickup device 22 and the light guide 23 can be extended/retracted with respect to the outer sheath 11 by extending/retracting the mounting section 71.

As shown in FIG. 3, the respective tip portions of the image pickup device 22 and the light guide 23 protrude from the insertion section 3 to the tip portion thereof and are connected by a holder 80. Hence, the mounting section 71 can be pulled back until the holder 80 makes contact with the end cap 13. When the mounting section 71 is extended, the mounting section 71 can be moved until it makes contact with the contact section 54B formed on a surface of the base portion of the supporting section 54. In other words, the image pickup device 22 can be extended/retracted in this range.

Figure 8:
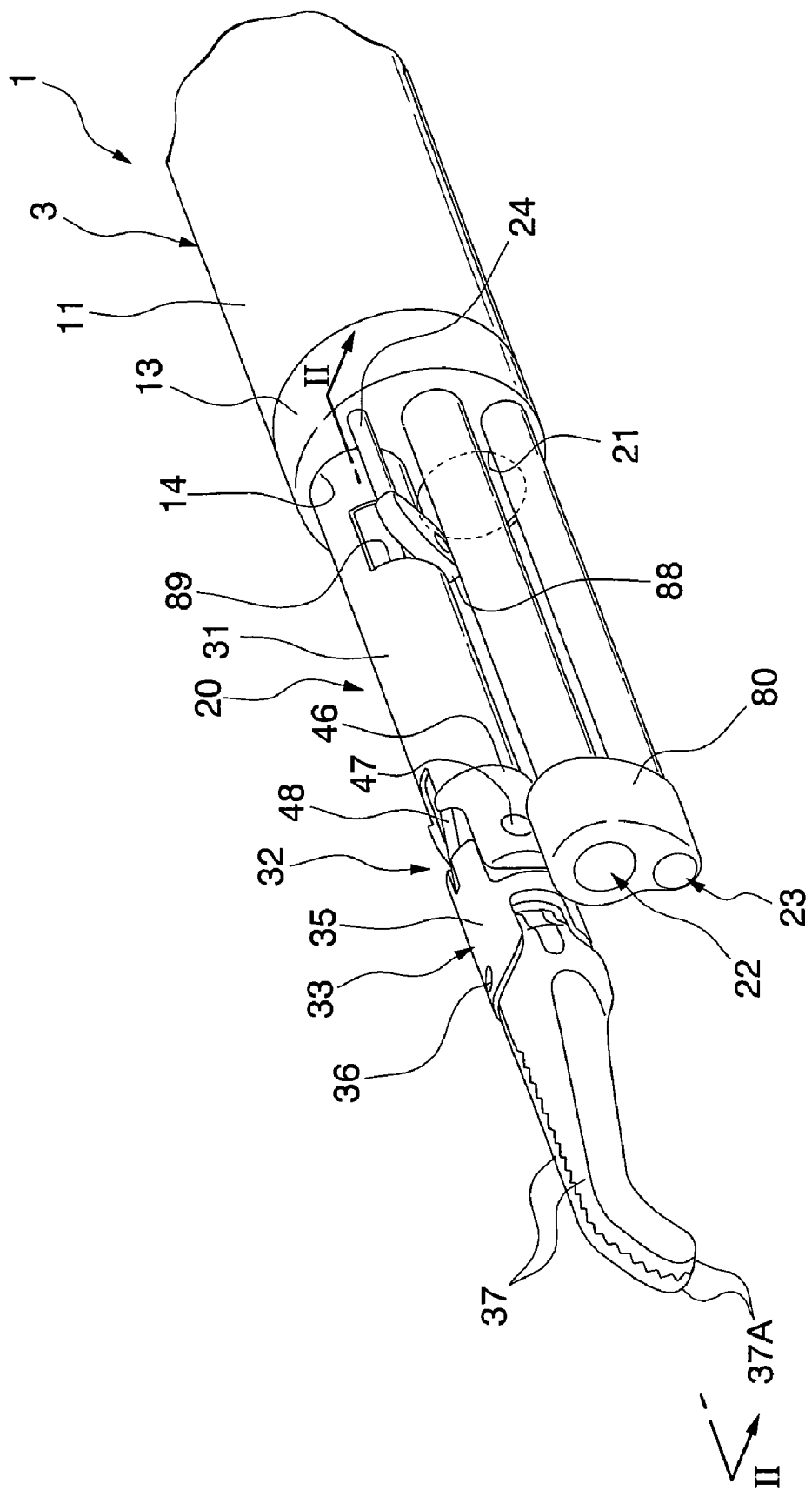
FIG. 8 is a perspective view showing an image pickup device and a lighting device having been extended from the state shown in FIG. 3.

FIG. 8 shows the position of the image pickup device 22 and the light guide 23 at the time when the mounting section 71 makes contact with the contact section 54B. This position is located closer to the base portion than the position of the forceps members 37 of the pivotable forceps 20 even when the image pickup device 22 and the light guide 23 are protruded most. The position is located more on the base portion than the position of the treatment section of the forceps 37 described later.

Figure 9:
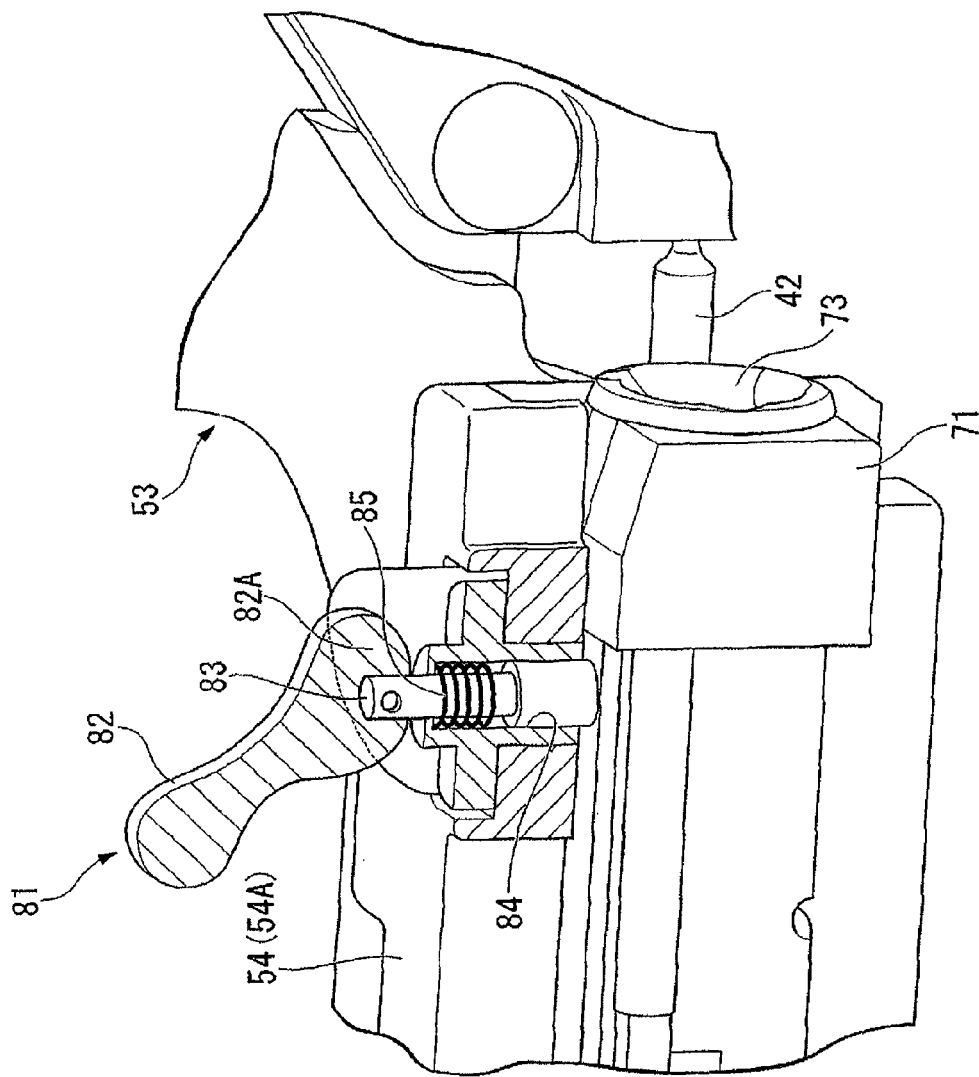
FIG. 9 is a sectional view taken along line IX-IX in FIG. 5 showing the configuration of the switching mechanism of the operation section.

In the movement path of the mounting section 71, a switching device 81 for restricting the movement of the mounting section 71 is provided. The switching mechanism 81 has a lever 82, the base portion of which is rotatably supported on the supporting section 54 by a pin 83. As shown in FIG. 9, a slot 82A is formed in the base portion of the lever 82. The pin 83 is disposed in the slot 82A so that one end of the pin 83 is connected to the lever 82. The other end of the pin 83 is inserted into a through hole 84 formed in the supporting section 54 so as to freely extend/retract. The through hole 84 is open in the direction of the movement path of the mounting section 71. The pin 83 is urged using a coil spring 85 toward the lever 82. When the lever 82 is raised, the pin 83 sinks into the supporting section 54 and retracts from the movement path of the mounting section 71. When the lever 82 is tilted as shown in FIG. 9, the tip portion of the pin 83 protrudes toward the movement path of the mounting section 71.

The operation section 2 is provided with an operation section for operating the wiper 24. As shown in FIG. 6, the operation section 87 for operating the wiper 24 is disposed on the base portion of the end cap 12 so as to protrude outward in the radial direction. When the operation section 87 is rotated, the wiper 24 is rotated. As shown in FIG. 3, the wiper 24 protrudes from the end cap 12, and a rubber piece 88 is provided at the tip portion thereof. The rubber piece 88 can be accommodated in a notch 89 formed on the side portion of the supporting tube 31 of the pivotable forceps 20. The rubber piece 88 and the notch 89 are disposed so that when the image pickup device 22 is retracted most, the surface of base portion of the rubber piece 88 can wipe the lens face of the image pickup device 22 by rotating the operation section 87.

Figure 10:
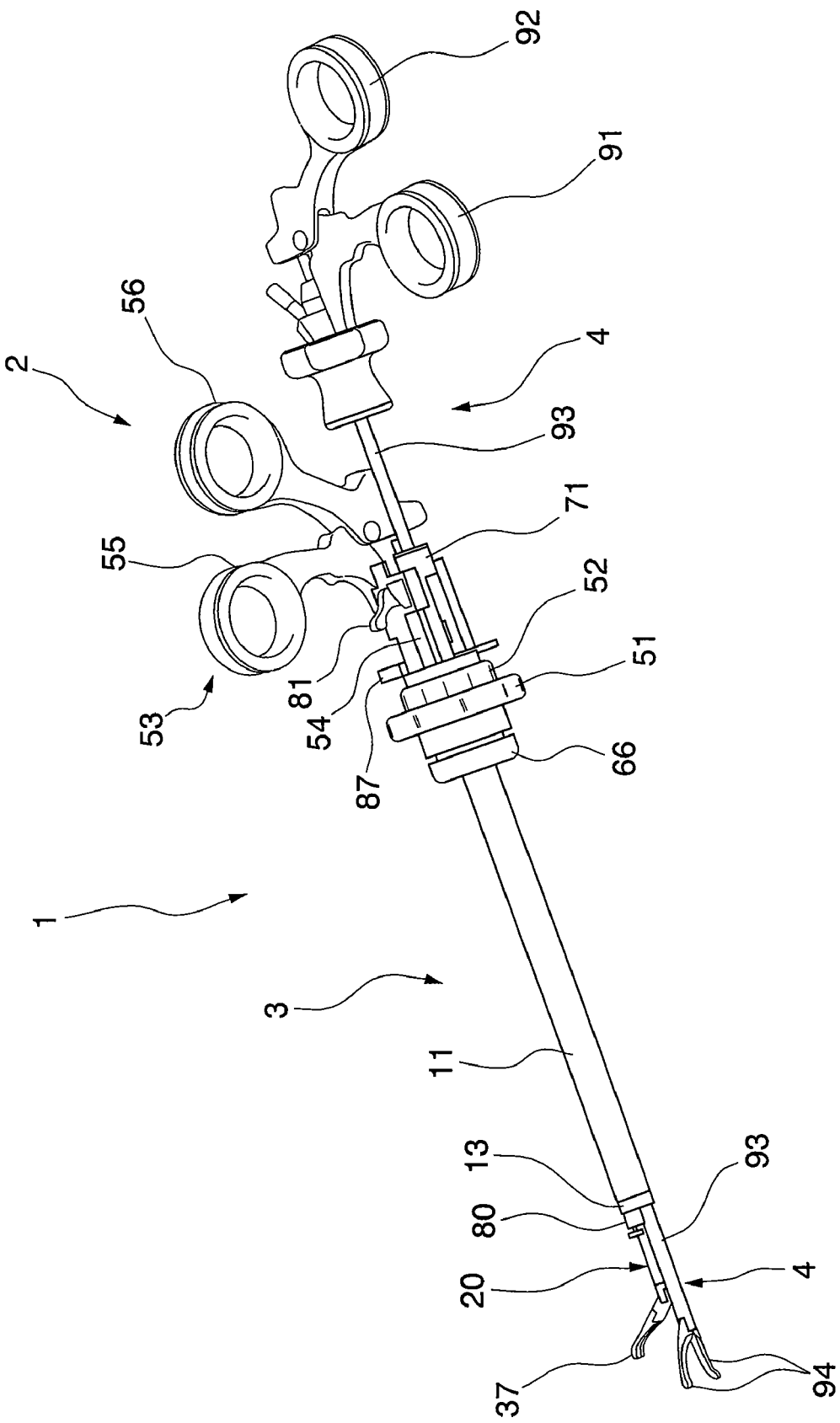
FIG. 10 is a perspective view taken from the direction B in FIG. 1.

As shown in FIG. 10, the forceps 4 that are replaceably inserted into the working channel 21 are provided with a pair of handles 91 and 92 at the base portion thereof so that the handles 91 and 92 freely open/close. A long, thin and hard sheath 93 is secured to the handle 91. The sheath 93 is passed through the mounting section 71 and inserted into the working channel 21. A pair of forceps members 94 are supported so as to freely open/close at the tip portion of the sheath 93 protruding from the insertion section 3. The pair of forceps members 94 can be opened/closed by the handles 91 and 92.

It is desirable that the forceps 4 be configured so that the pair of handles 91 and 92 are disposed in a direction different from that of the handles 55 and 56 of the forceps 20 when the forceps 20 are disposed upward, the working channel 21 is disposed downward, and the opening/closing direction of the forceps members 94 is set to a direction substantially orthogonal to the bending direction of the forceps 4. In particular, when the handles 91 and 92 of the forceps 4 are disposed at a position shifted by 90° or 180° around the axis line with respect to the handles 55 and 56 of the forceps 4, the operation is made easy.

The control unit 5 shown in FIG. 1 is constituted of an image processing section 7 for displaying images taken using the image pickup device 22 on a screen, a light source 8 to which the light guide 23 is connected, and an air/water supply device 9.

Next, the action of this embodiment will be described below, taking a case in which a tumor is removed as an example.

Figure 11:
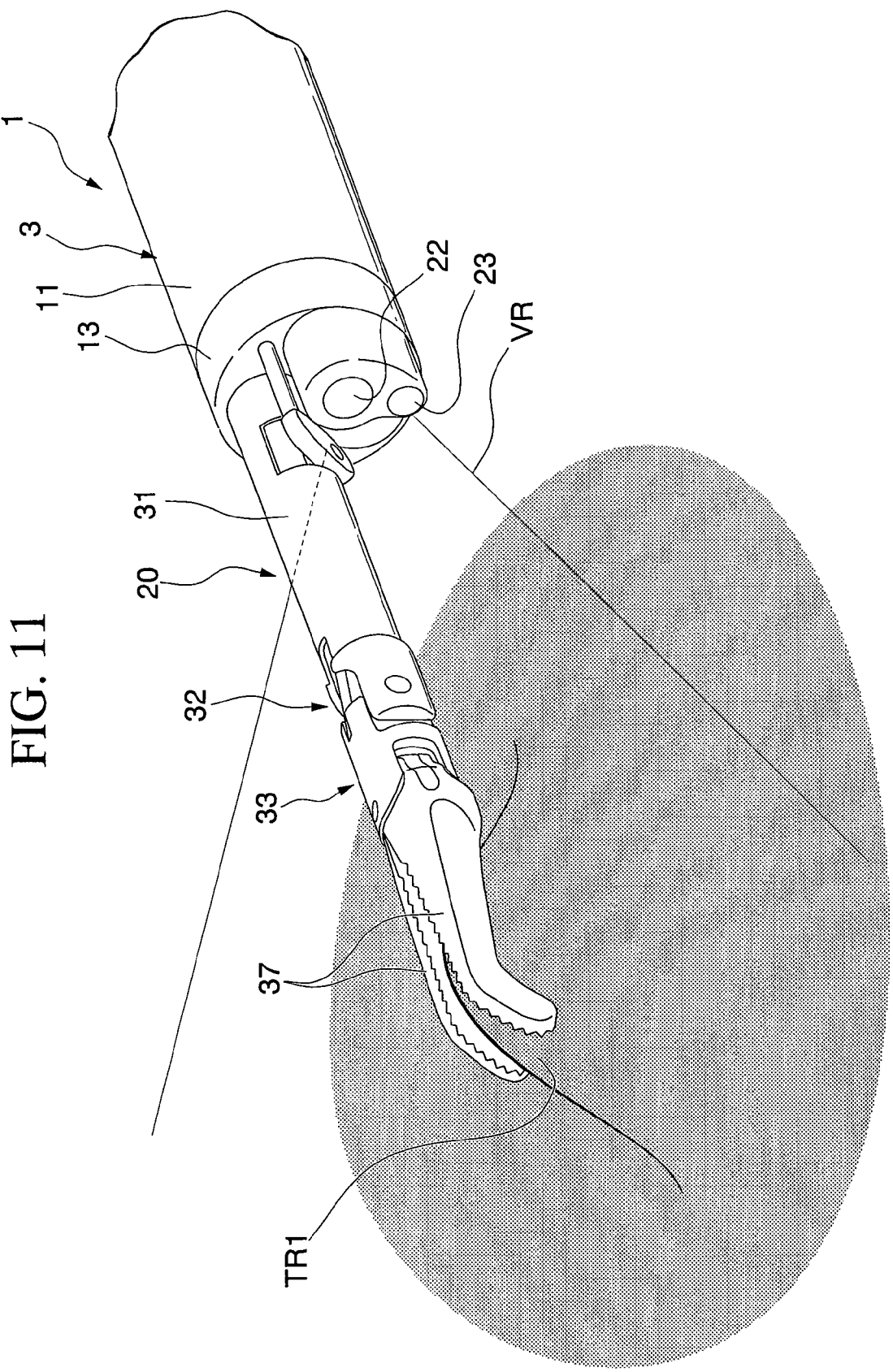
FIG. 11 is a view illustrating a treatment procedure, a tumor being held with forceps.

An opening is formed in a body cavity, a trocar is inserted, and then the insertion section 3 of the surgical treatment apparatus 1 is inserted into the body cavity. At this time, as shown in FIG. 3, the treatment section 33 of the pivotable forceps 20 is inserted while being extended in the axial direction, the interior of the body cavity is illuminated using the light guide 23, and images of the interior of the body cavity are taken using the image pickup device 22. The images of the interior of the body cavity are processed using the image processing section 7 of the control unit 5 and displayed on a monitor 6. The forceps members 37 are opened/closed by operating the pair of handles 55 and 56 so that a tumor TR1 is held with the pair of forceps members 37 as shown in FIG. 11. At this time, the tumor TR1 can be reliably held because the forceps members 37 are located in the visual range VR of the image pickup device 22.

Figure 12:
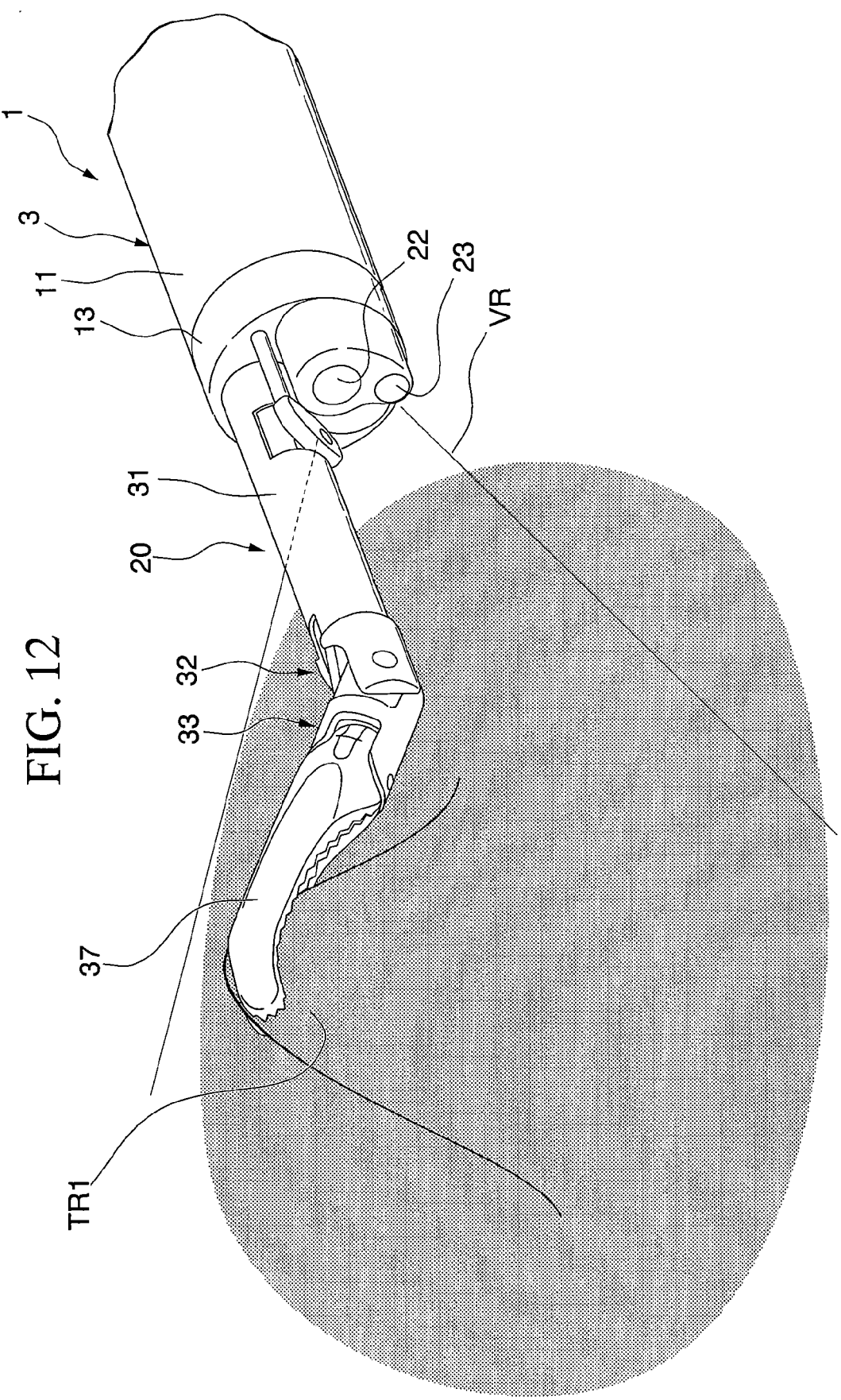
FIG. 12 is a view showing a state in which the tip portion of the forceps holding the tumor are rotated to lift the tumor.

Rotating of the first knob 51 in a direction returning to the operator while the tumor TR1 is held moves the pin 67 shown in FIG. 7 and bends the bending operation member 48 in the retracting direction. Since the tip portion of the bending operation member 48 is connected to the treatment section 33, the treatment section 33 is rotated with respect to the supporting tube 31 so as to be bent up. Hence, the tumor TR1 being held by the forceps members 37 is pulled as shown in FIG. 12. The state in which the tumor TR1 is pulled can be checked using the image pickup device 22.

Next, the forceps 4 for removing the tumor TR1 are inserted into the working channel 21. First, the switching device 81 shown in FIG. 9 is set to the ON state, that is, the state in which the pin 83 is protruded. The sheath 93 of the forceps 4 is press-inserted into the mounting section 71. The insertion stops when the mounting section 71 makes contact with the pin 83. When the tip portion of the forceps 4 is inserted into the body cavity beyond the image pickup device 22, the switching lever 82 is raised so that the pin 83 is sunk into the supporting section 54. When the forceps 4 are extended, the image pickup device 22 and the light guide 23 are extended together with the mounting section 71. Since the sheath 93 of the forceps 4 and the mounting section 71 can be moved integrally by virtue of the elastic member 74, the image pickup device 22 follows the extending/retracting operation of the forceps 4. As a result, it is possible to obtain close-up detailed images of the forceps members 94 and the surrounding area.

Figure 13:
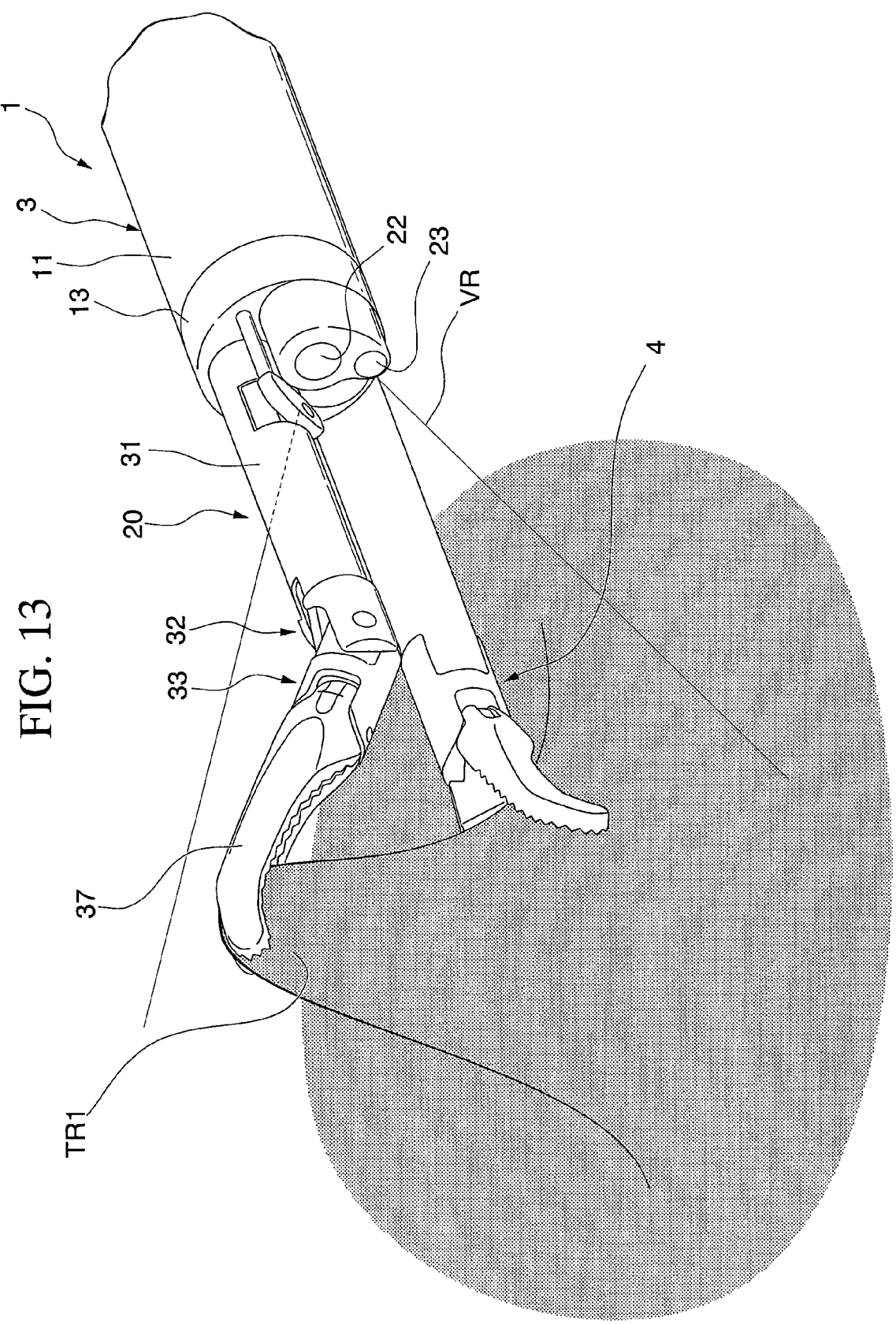
FIG. 13 is a view showing a state in which a treatment instrument is inserted.
Figure 14:
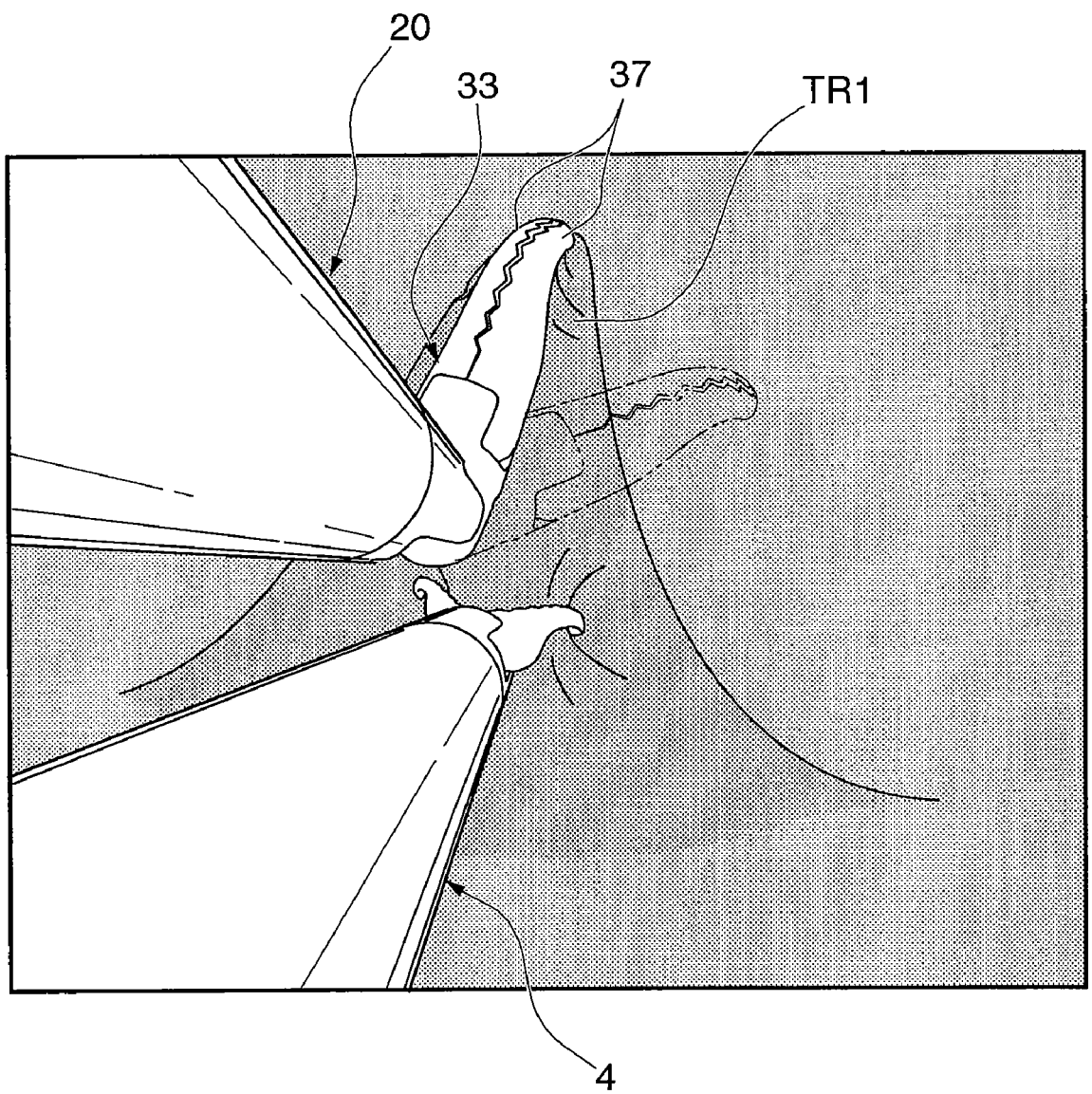
FIG. 14 is a schematic view showing an image of the interior of the body cavity taken by the image pickup device in the state shown in FIG. 13.

As shown in FIG. 13, the central portion of the tumor TR1 being nipped and lifted with the pivotable forceps 20 is located ahead of the forceps 4. While this state is maintained, the forceps 4 are extended, and the forceps members 94 are opened/closed by operating the handles 91 and 92 of the forceps 4, whereby the tumor TR1 can be removed using the forceps 4. At this time, as shown in FIG. 14, the tip portion of the pivotable forceps 20, the tip portion of the forceps 4, and the tumor TR1 to be treated can be checked on the monitor 6 without being obstructed from one another. When close-up images are desired, the mounting section 71 should only be extended relatively with respect to the forceps 4. When remote images are desired, the mounting section 71 should be retracted relatively with respect to the forceps 4.

Figure 15:
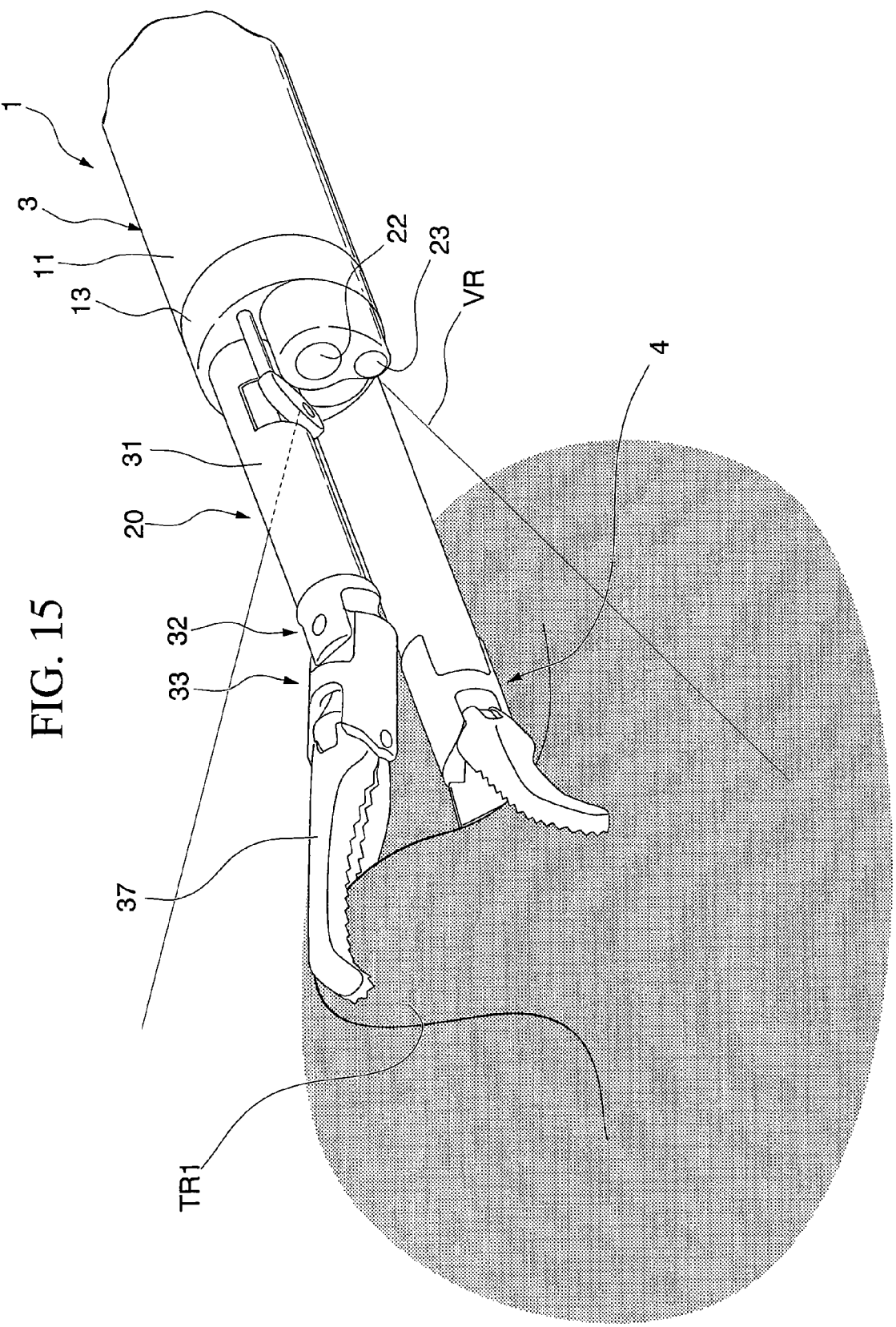
FIG. 15 is a view showing a state in which the forceps lifting the tumor is rotated.

When the tumor TR1 located at a position away from the axis line of the forceps 4 is cut off, the second knob 52 is rotated. The pins 60 of the second knob 52, shown in FIG. 6, are engaged with the pin 61 extending from the supporting tube 31 and rotate the supporting tube 31. As shown in FIG. 15, the pivotable forceps 20 are rotated as a whole around the axis line of the supporting tube 31, and the tumor TR1 being held by the forceps members 37 disposed at the tip portion of the instrument is pulled in the rotation direction. As a result, the peripheral portion of the tumor TR1 on the opposite side of the rotation direction is pulled into the operation range of the forceps 4. Hence, the portion can be cut by opening/closing the forceps members 94. In addition, the portion on the opposite side can also be cut similarly by rotating the second knob 52 in the opposite direction and by opening/closing the forceps members 94. After the cutting off of the tumor TR1 is completed, the image pickup device 22 is used to check for any remaining tumors. The first knob 51 is then rotated to return the treatment section 33 to its original position, and the surgical treatment apparatus 1 is extracted from the body cavity. The tumor TR1 being held by the pivotable forceps 20 is taken out to the outside of the body.

It may be possible that the forceps 4 are installed in advance in the surgical treatment apparatus 1. Depending on the requirements of treatment, it may be possible that the forceps 4 are extracted and a clip is inserted to anastomose the incised portion. It may also be possible that a local injection needle is inserted so that the tumor TR1 is bulged with physiological saline beforehand.

Furthermore, when the forceps 4 are thrust while the pin 83 of the switching device 81 is protruded, only the forceps 4 can be extended while the position of the image pickup device 22 remains unchanged. This is effective when it is desired to check the whole state using a wide-ranging image. Still further, it may also be possible that the image pickup device 22 is provided with an optical zooming function or that the image processing section 7 is provided with an electronic zooming function so that the observation range can be adjusted.

In this embodiment, treatment can be carried out using two treatment instruments. Furthermore, since the surgical treatment apparatus is provided with the image pickup device 22, treatment can be carried out only by inserting one apparatus into the body. For example, in conventional transurethral treatment, it was impossible to carry out treatment while checking the state of the treatment. However, in this embodiment, this kind of problem can be solved. Furthermore, even when the location in which openings are formed is limited, such as in the treatment of the mediastinum of the lung, the number of apparatuses to be inserted can be reduced, and the treatment made easy. Since the image pickup device 22 is disposed between the treatment instruments, the image pickup device 22 can view the pivotable forceps 20 and the like without obstruction, whereby the treatment is made easy. Since the image pickup device 22 is located at a position offset from the pivotable forceps 20 and the working channel 21, the outside diameter of the insertion section 3 can be made smaller than that when the three ducts are arranged linearly.

Since the pivotable forceps 20 can be bent and rotated as described above, treatment is facilitated even when the approach angle thereof in the body cavity is restricted. Since the bending and rotating can be operated by rotating the knobs 51 and 52, the operability is improved. In contrast to the pivotable forceps 20 being offset from the axis line of the outer sheath 11, the rotation centers of the knobs 51 and 52 are aligned with the axis line of the outer sheath 11, whereby the operability is high. In addition, since the image pickup device 22 can be extended/retracted in conjunction with the forceps 4 using the mounting section 71, images around the forceps 4 can be taken more securely.

Figure 16:
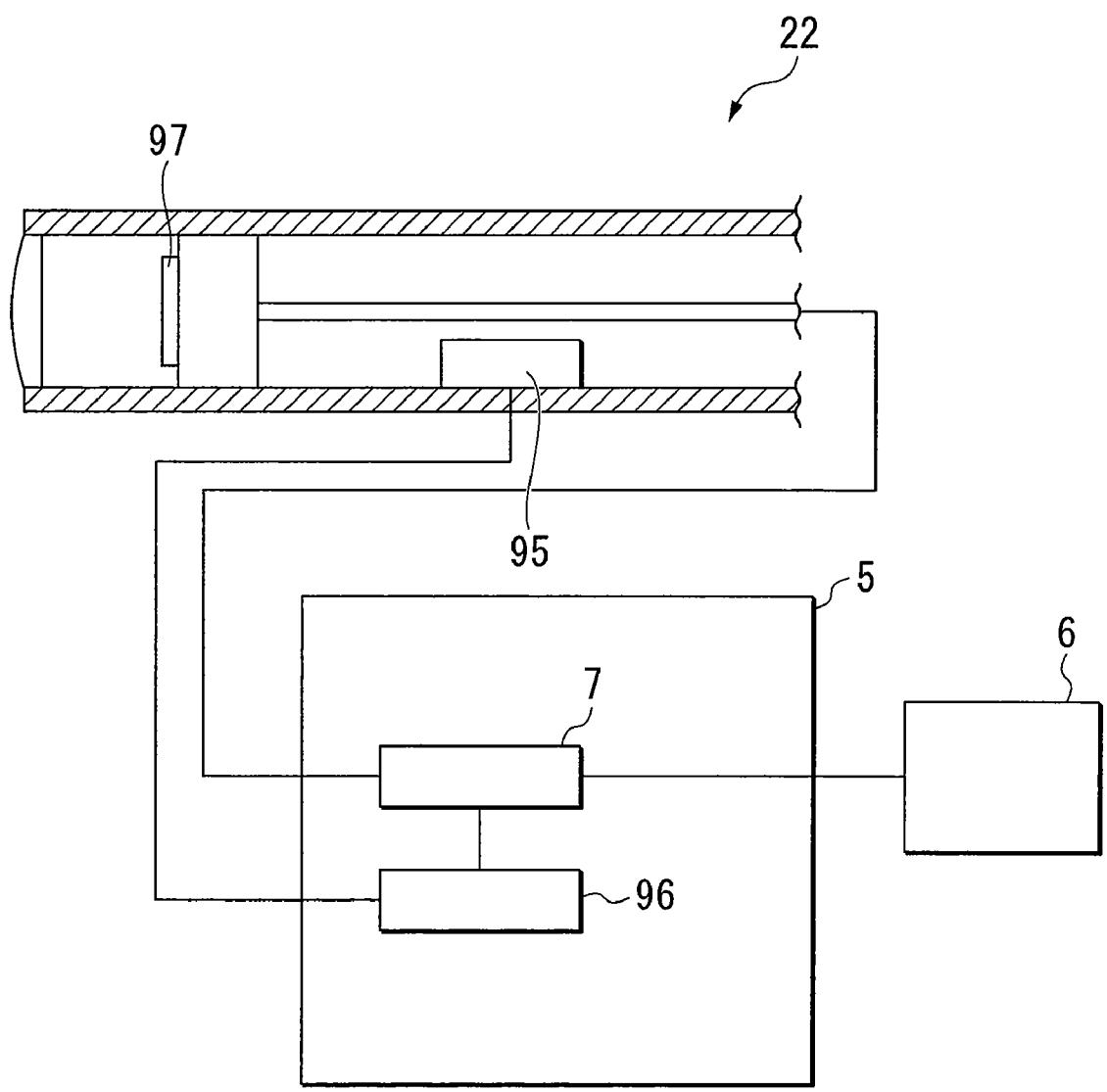
FIG. 16 is a view showing a schematic configuration in which the image pickup device is provided with a rotation detector and a controller is provided with a correction device.

Modification examples of this embodiment will be described below. As shown in FIG. 16, the image pickup device 22 may be provided with a rotation detector 95 (for example, an acceleration sensor). With the rotation detector 95, even when the surgical treatment apparatus 1 is rotated around the axis line, the observation image can always have a constant orientation. For example, the vertical direction of the observation image can be maintained so as to remain unchanged. In this case, the angle detector 96 of the control unit 5 calculates the amount of change in the rotation direction on the basis of the output signal from the rotation detector 95. Then, the image processing section 7 carries out image processing so as to cancel the amount of change. With a correction device including the angle detector 96 and the image processing section 7, an image having no change in the rotation direction can be obtained on the monitor 6, and treatment is made easy. Furthermore, when an image sensor 97, such as a CCD, is installed so as to be freely rotated using a motor, the image sensor 97 can be rotated so that the amount of change in the rotation direction, calculated using the control unit 5, is canceled. In this case, an image having no change in the rotation direction can also be obtained on the monitor 6. Since no relative change occurs in the vertical direction during treatment, manipulation is made easy.

Figure 17:
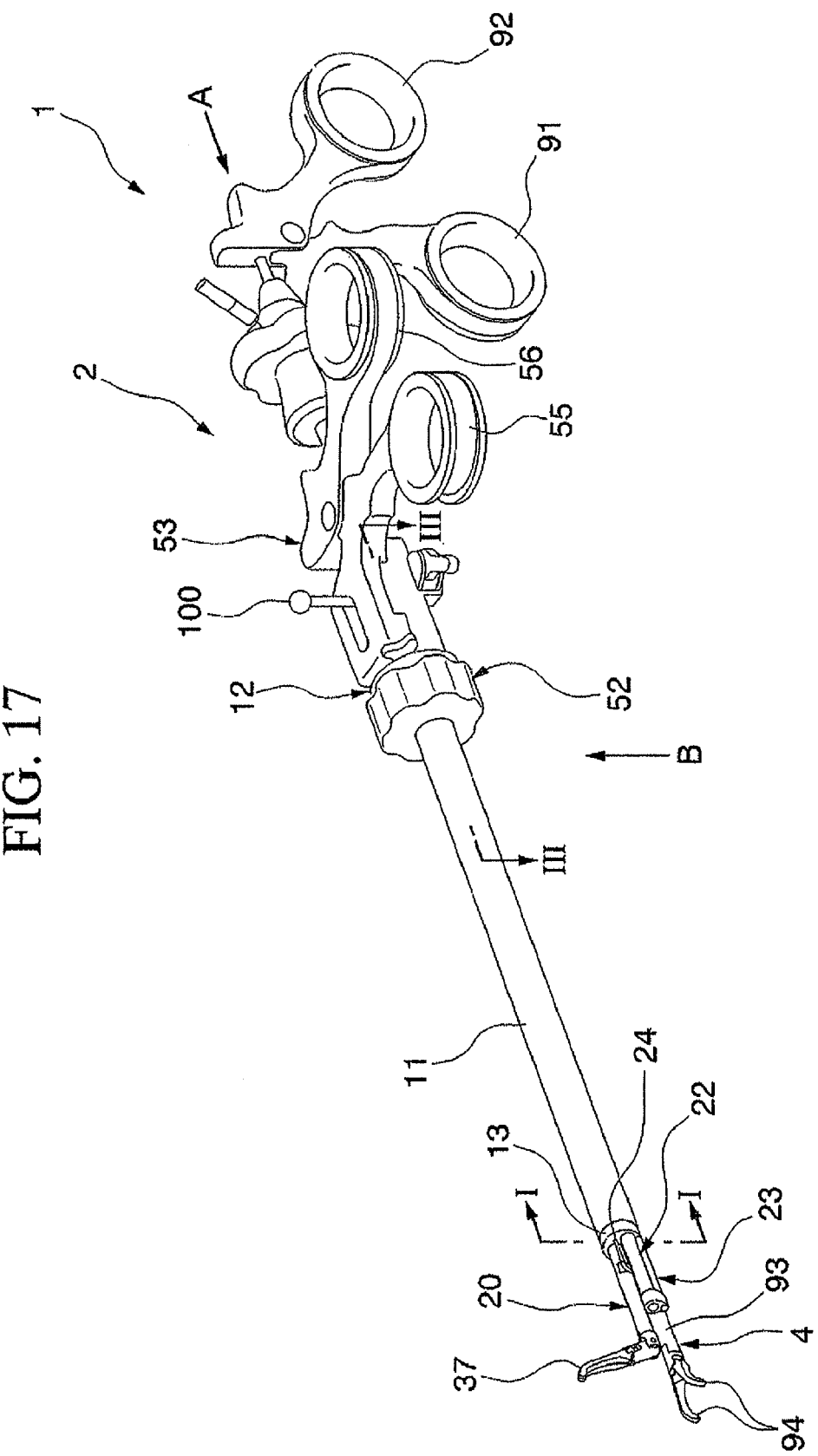
FIG. 17 is a perspective view showing a configuration in which a lever is provided instead of a first knob.

Still further, such a lever 100 as shown in FIG. 17 may also be used instead of the first knob 51. The lever 100 is disposed in a groove formed in the longitudinal direction of the supporting section 54 so as to freely extend/retract and is connected to the bending operation member 48. When the lever 100 is pulled, the treatment section 33 is bent; when the lever 100 is pushed, the treatment section 33 is returned. The second knob 52 may also be embodied in the form of a lever.

Figure 18:
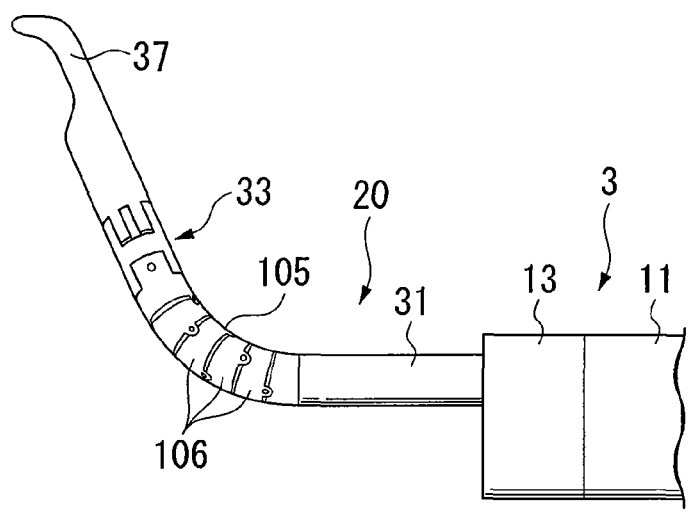
FIG. 18 is a view showing a configuration in which the joint of the forceps can be bent.

As shown in FIG. 18, a bendable joint 105 may also be provided. The joint 105 is constituted of a plurality of bending pieces 106 connected in the longitudinal direction. A wire (not shown) is passed in the outer circumferential portions of the respective bending pieces 106 of the joint 105, the outer circumferential portions being away from the working channel 21. The wire is secured to the bending piece 106 disposed at the tip portion of the joint 105. When the wire is pulled, the joint 105 is curved and the treatment section 33 is bent away from the axis line.

Figure 19:
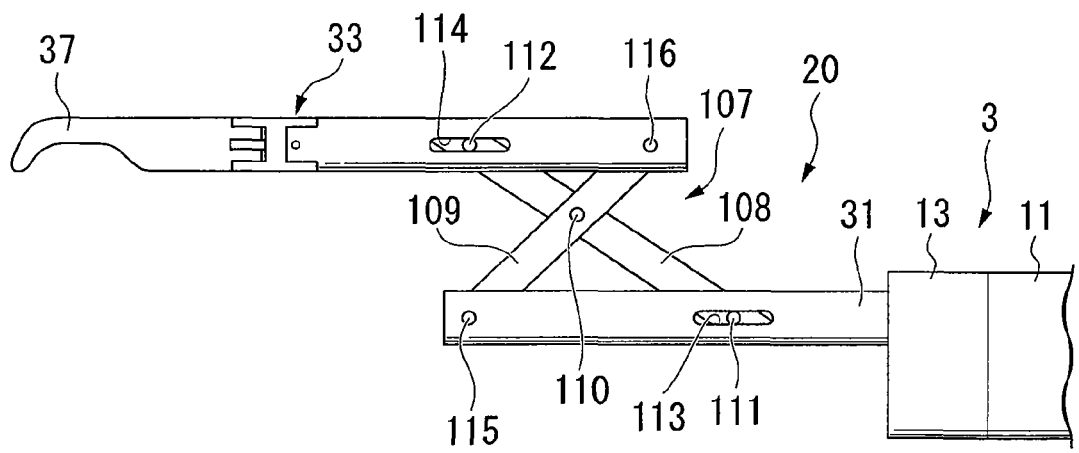
FIG. 19 is a view showing forceps capable of being offset.

As shown in FIG. 19, an offset device 107 for offsetting the treatment section 33 with respect to the supporting tube 31 may also be provided. The offset device 107 is configured so that a first lever 108 and a second lever 109 are connected using a pin 110 so as to intersect each other. The two end portions of the first lever 108 are inserted into the supporting tube 31 and the treatment section 33, respectively. Furthermore, the two end portions of the first lever 108 are provided with pins 111 and 112 secured thereto, respectively. The pin 111 is freely slidably supported in the groove 113 formed in the supporting tube 31. The pin 112 is freely slidably supported in the groove 114 formed in the treatment section 33. The two end portions of the second lever 109 are supported using pins 115 and 116 so as to be freely rotatable with respect to the supporting tube 31 and the treatment section 33, respectively. The offset device 107 is folded in its initial state, and the treatment section 33 is disposed substantially linearly. When the end portion of the first lever 108 is pushed forward by operating the operation section (for example, the first knob 51), the offset device 107 is unfolded, and the treatment section 33 is moved to a position offset from the axis line.

Even in these modification examples, effects similar to those described above are obtained. Structures having no rotation mechanism and configurations that do not raise may also be used, provided that the purpose of the manipulation can be attained.

Second Embodiment

Figure 20:
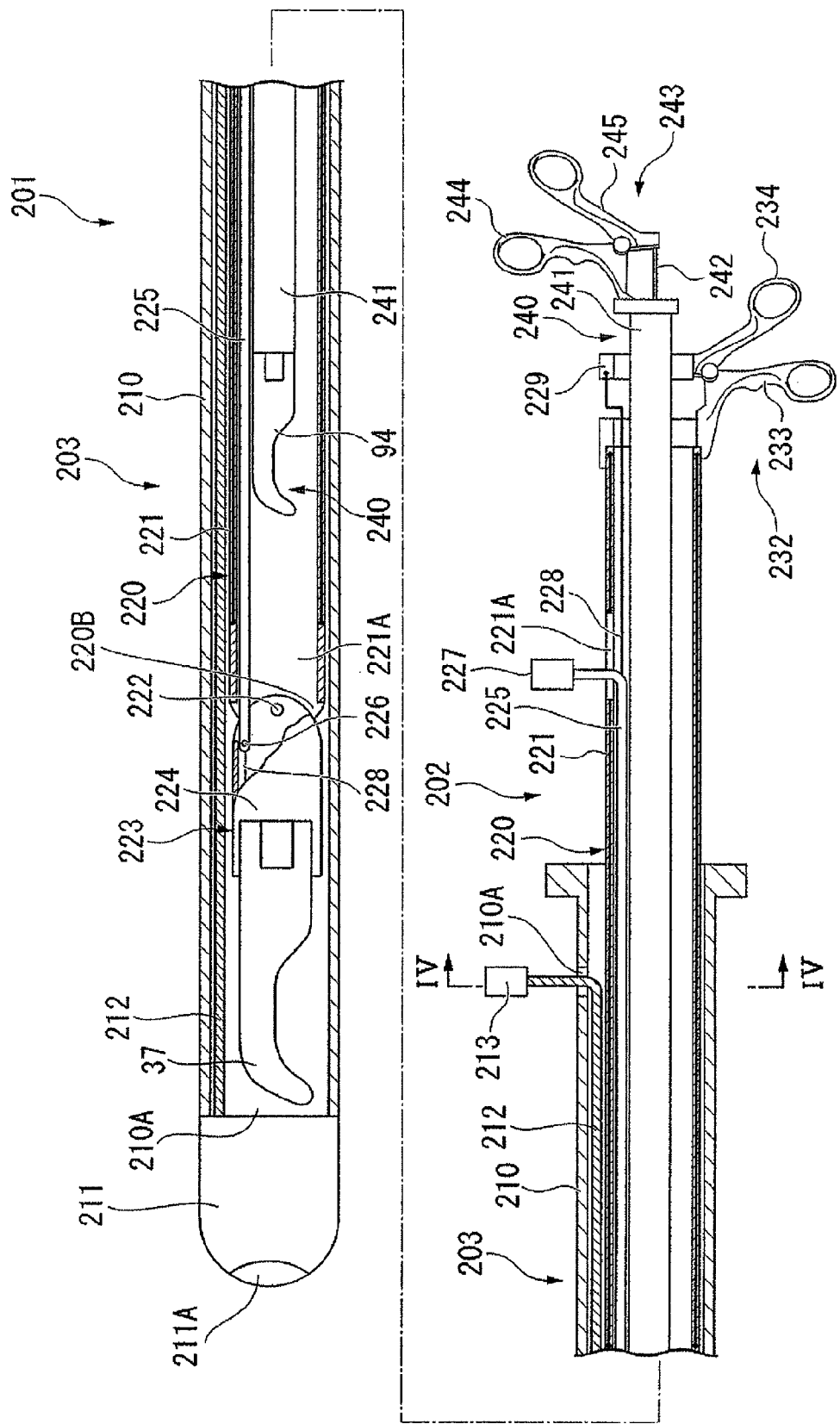
FIG. 20 is a sectional view showing a configuration in which the forceps and the image pickup device are disposed on the axis line of the outer sheath.

This embodiment is characterized in that two treatment instruments and an image pickup device can be disposed concentrically with one another. As shown in FIG. 20, in a surgical treatment apparatus 201, a long, thin and hard insertion section 203 extends from an operation section 202 that is operated outside the body by the operator. The insertion section 203 has a cylindrical outer sheath 210, and an image pickup device 211 is disposed at the tip portion thereof that is inserted into the body. The outside diameter of the image pickup device 211 is substantially equal to that of the outer sheath 210, and the image pickup device 211 provides illumination and takes images through a transparent cover 211A disposed at the tip portion thereof. The image pickup device 211 is supported using a rotation rod 212 passed through the outer sheath 210. The rotation rod 212 is freely rotatably passed through at a position near the inner circumferential face and offset from the axis line of the outer sheath 210. The rotation rod 212 is bent and drawn out from a slit 210A formed on the base portion of the outer sheath 210, and a knob 213 is secured to the end portion thereof so as to be held by the operator and to serve as an operation section. The base portion of the outer sheath 210 is diametrically expanded into a flange shape so as to be held easily by the operator.

Figure 21:
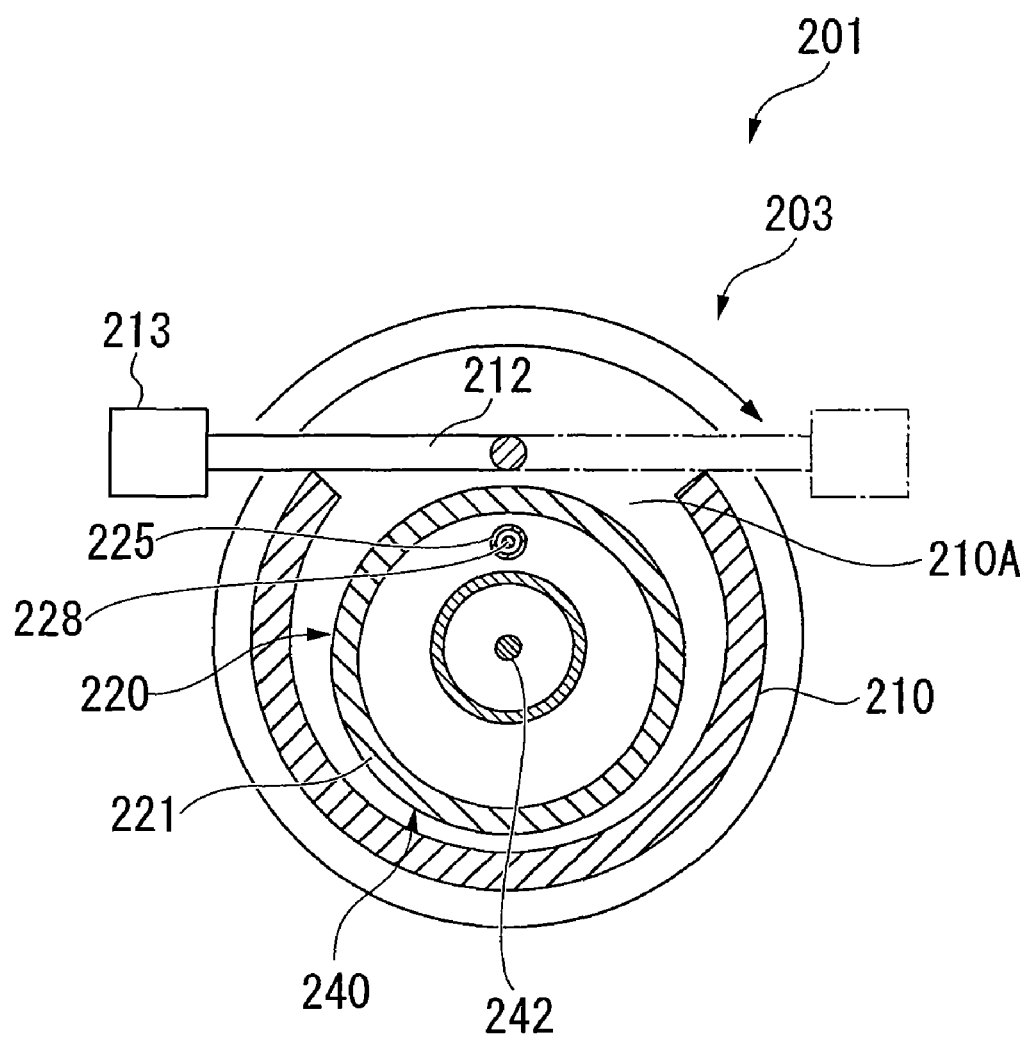
FIG. 21 is a sectional view taken along line IV-IV in FIG. 20.
Figure 22:
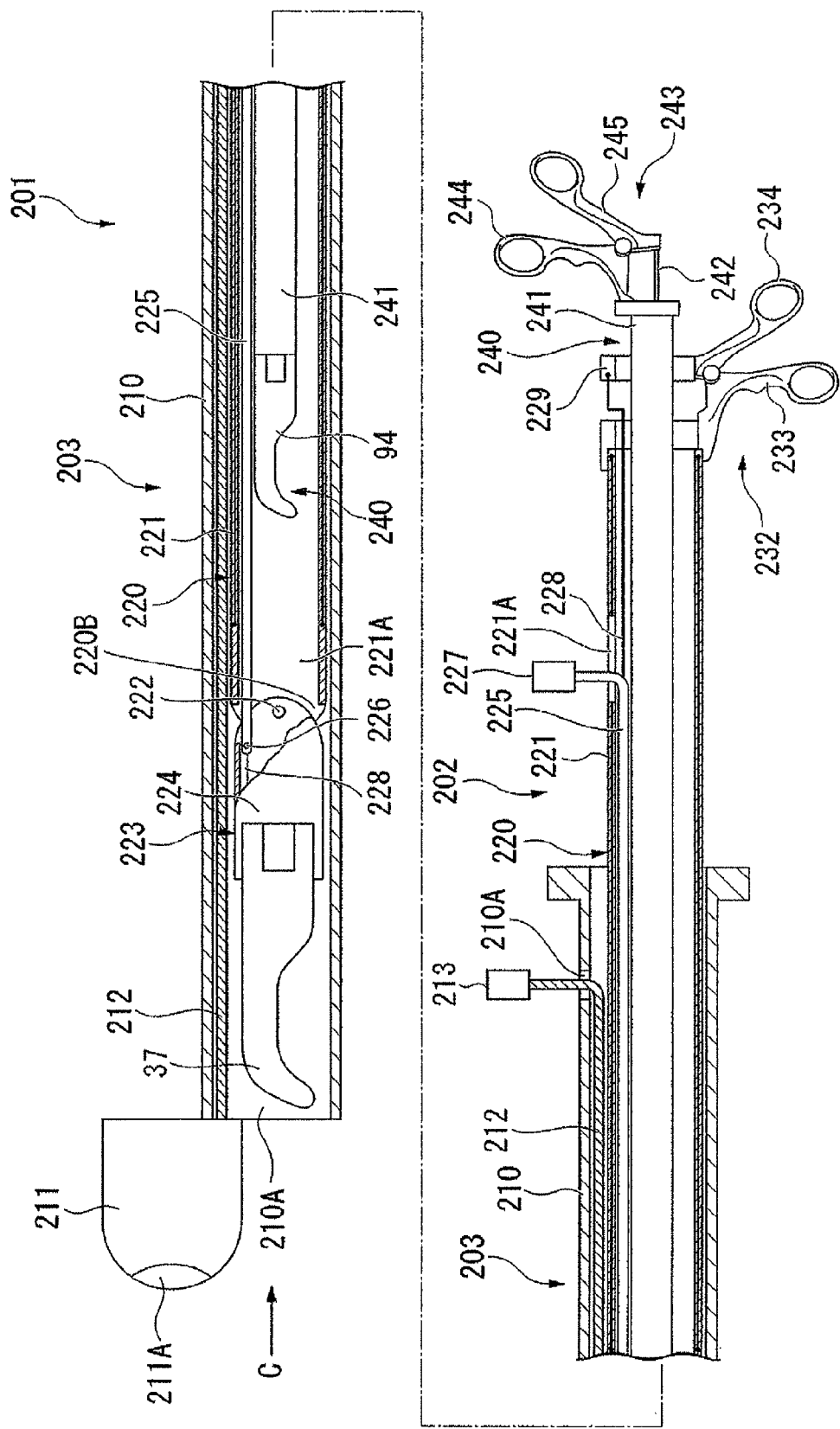
FIG. 22 is a view showing a state in which the image pickup device is moved to its offset position.
Figure 23:
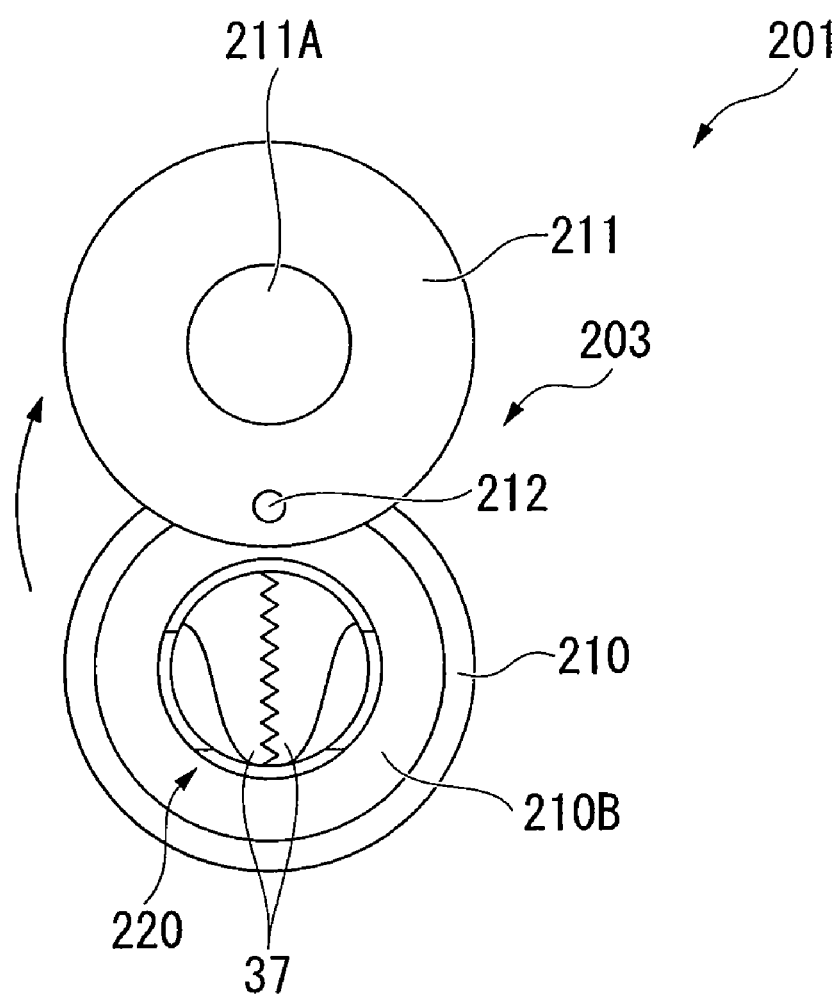
FIG. 23 is a view taken from arrow C of FIG. 22.

As shown in FIG. 21, the slit 210A extends in the circumferential direction. When the rotation rod 212 is shifted to one end portion of the slit 210A, the image pickup device 211 closes the tip portion opening 210B of the outer sheath 210 and is disposed concentrically therewith. When the knob 213 is moved to the opposite end portion of the slit 210A as indicated by imaginary lines, the image pickup device 211 is rotated around the rotation rod 212. As shown in FIG. 22 and FIG. 23, the image pickup device 211 is offset with respect to the outer sheath 210, and the tip portion opening 210B of the outer sheath 210 is opened. The image pickup device 211 can be rotated easily by providing a supporting member or a lumen, not shown, for the outer sheath 210 so as to freely rotatably support the rotation rod 212.

Pivotable forceps 220 are passed through the outer sheath 210 so as to freely extend/retract. The pivotable forceps 220 have a hollow sheath 221. A pin 222 is secured to the circumferential wall of the tip portion opening 210B of the sheath 221, and a treatment section 223 is freely rotatably installed via the pin 222. The pin 222 is disposed so as not to close the tip portion opening 210B.

Figure 24:
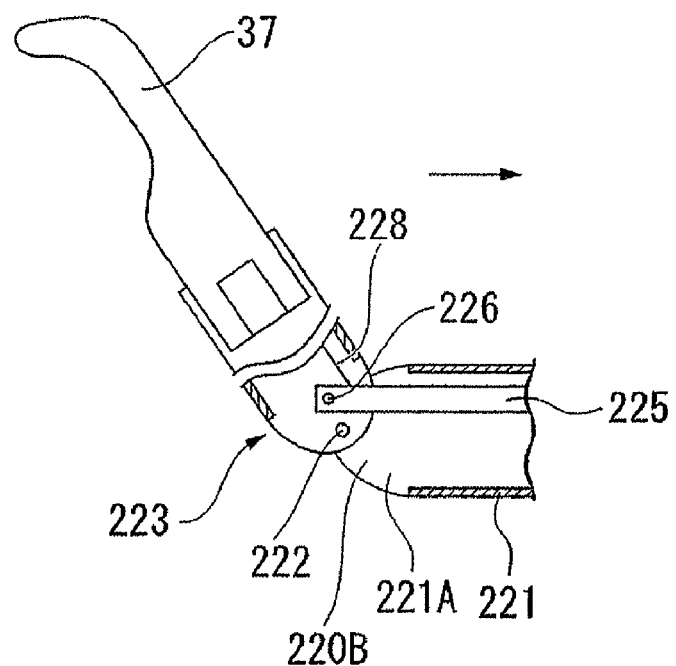
FIG. 24 is a view showing a state in which the treatment section of the pivotable forceps are bent.

In the treatment section 223, the pair of forceps members 37 is supported on a supporting member 224 so as to freely open/close. The opening/closing direction of the forceps members 37 is substantially orthogonal to the bending direction of the treatment section 223 around the pin 222. A pulling pipe 225 is connected to the base portion of the treatment section 223 via a pin 226. The pulling pipe 225 is passed through the sheath 221 so as to freely extend/retract at a position offset from the axis line of the pivotable forceps 220 in the same direction as that of the rotation rod 212 and is drawn out from a slit 221A formed near the operator. The slit 221A extends in the axial direction. The pulling pipe 225 is bent outward so as to be aligned with the position at which the slit 221A is formed, and a knob 227 is secured to the end portion thereof so as to serve as an operation section. When the knob 227 is pulled, the treatment section 223 is bent upward as shown in FIG. 24.

Figure 25:
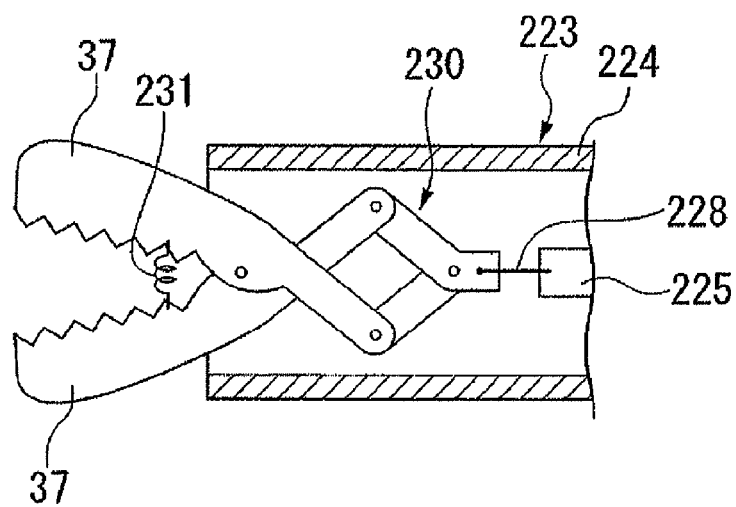
FIG. 25 is a sectional view showing the configuration of the treatment section of the pivotable forceps.

An opening/closing operation wire 228 is inserted from the bent portion of the pulling pipe 225 shown in FIG. 20. The opening/closing operation wire 228 is passed through the pulling pipe 225 so as to freely extend/retract and is pulled into the treatment section 223. As shown in FIG. 25, inside the treatment section 223, the opening/closing operation wire 228 is connected to a link mechanism 230 that is connected to the pair of forceps members 37. Since the forceps members 37 are urged so as to open using a spring 231, the pair of forceps members 37 can be closed by pulling a knob 229 connected to the opening/closing operation wire 228 toward the operator. When the knob 229 is released, the forceps members 37 are opened by the action of the spring 231. At the base portion of the sheath 221, the knob 229 is connected to a handle 234 that can be opened/closed, one of a pair of handles 233 and 234 provided so as to serve as an operation section 232. When the handles 233 and 234 are released, the forceps members 37 are opened; when the handles 233 and 234 are squeezed, the forceps members 37 are closed.

Into the sheath 221 of the pivotable forceps 220, forceps 240 are inserted so as to freely extend/retract as a replaceable treatment instrument. The pair of forceps 240 is supported at the tip portion of a sheath 241 so that the pair of forceps members 94 thereof freely open/close. The forceps members 94 can be opened/closed by extending/retracting a rod 242 passed through the sheath 241. The rod 242 can be extended/retracted by opening/closing of handles 244 and 245 of the operation section 243 provided at the base portion of the sheath 241.

When a medical practice is carried out, the outer sheath 210 and the image pickup device 211 are disposed concentrically, and the two forceps 220 and 240, having been inserted into the outer sheath 210, are introduced into the body. The interior of the body is observed using the image pickup device 211. When the target region is reached, the knob 213 of the rotation rod 212 is operated to rotate the image pickup device 211. Hence, the image pickup device 211 is disposed so as to be offset with respect to the outer sheath 210. Manipulation is then carried out while monitoring images obtained from the offset position.

Figure 26:
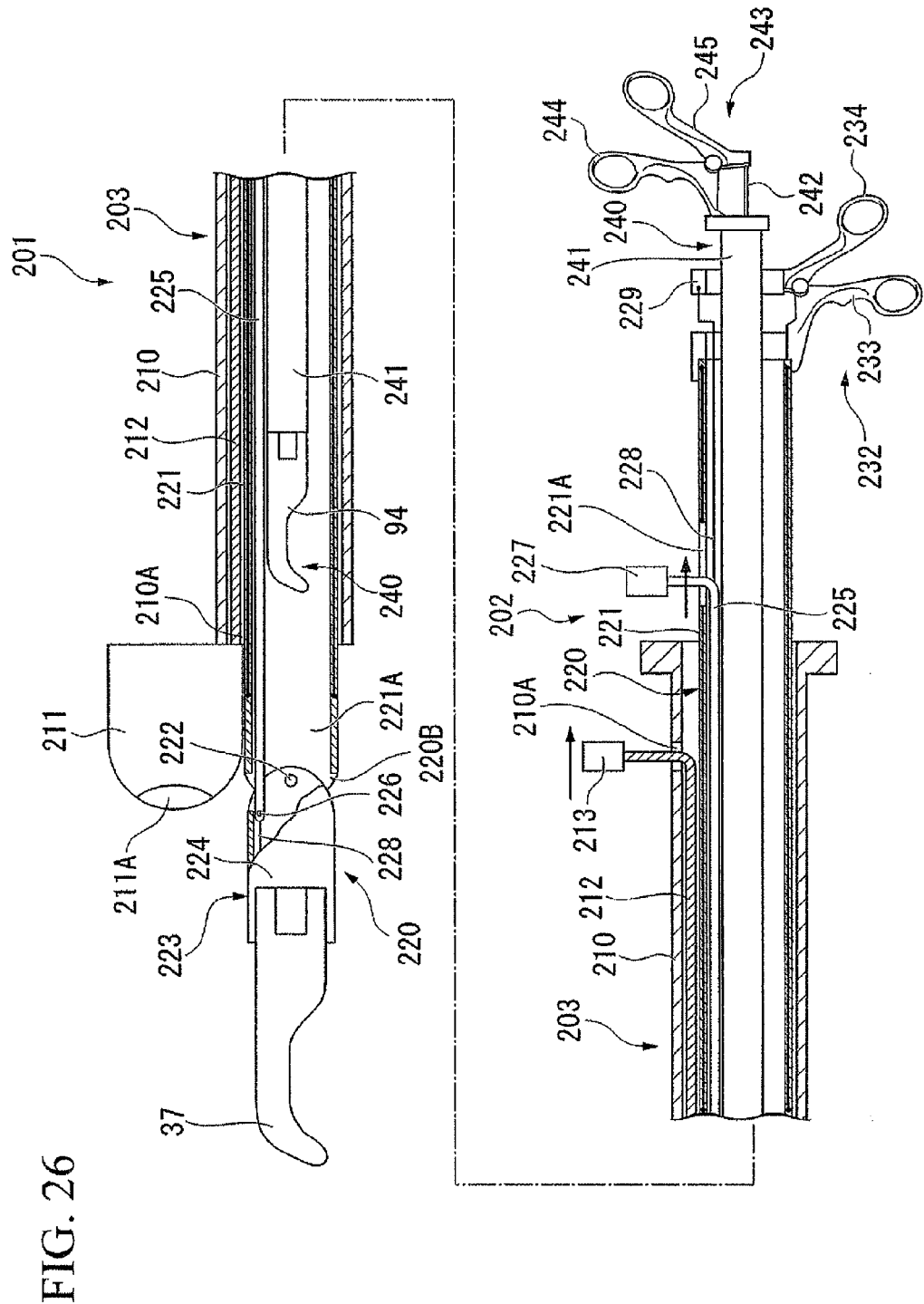
FIG. 26 is a view showing a state in which the outer sheath is retracted and the pivotable forceps are protruded.

The handles 233 and 234 of the operation section 232 of the pivotable forceps 220 are grasped and the outer sheath 210 is pulled toward the operator. As shown in FIG. 26, the outer sheath 210 approaches the operation section 232, and the pivotable forceps 220 are exposed from the tip portion opening 210B of the outer sheath 210. The pair of forceps members 37 are closed to grasp the tissue by pulling the knob 229 connected to the opening/closing operation wire 228. When the knob 227 of the pulling pipe 225 is pulled while the knob 229 is pulled, the joint is operated around the pin 222. As a result, the treatment section 223 is bent up toward the image pickup device 22, and the tissue is pulled.

Since the tip portion opening 210B formed in the sheath 221 of the pivotable forceps 220 is opened, the forceps 240 are extended, and the pair of forceps members 94 is protruded. The handles 244 and 245 are operated to cut the tissue. When the tissue located at a position away from the axis line of the forceps 4 is cut, the end portion of the outer sheath 210 is secured by hand, and the pivotable forceps 220 are rotated around the axis line. Although the tissue is pulled in the rotation direction of the pivotable forceps 220, the tissue being pulled into the operation range of the forceps 240 can be cut since the forceps 240 that are passed through the sheath 221 are not rotated.

Since the two forceps 220 and 240 can be disposed concentrically in this embodiment, the outside diameter of the outer sheath 210 can be made smaller. The surgical treatment apparatus can thus be inserted easily into the body, and necessary treatment can be carried out even if operation space is limited. Since the image pickup device 211 can be disposed concentrically with the outer sheath 210, the image pickup device 211 can be inserted easily into the body. The effects of using the apparatus for treatment are the same as those in the first embodiment.

Figure 27:
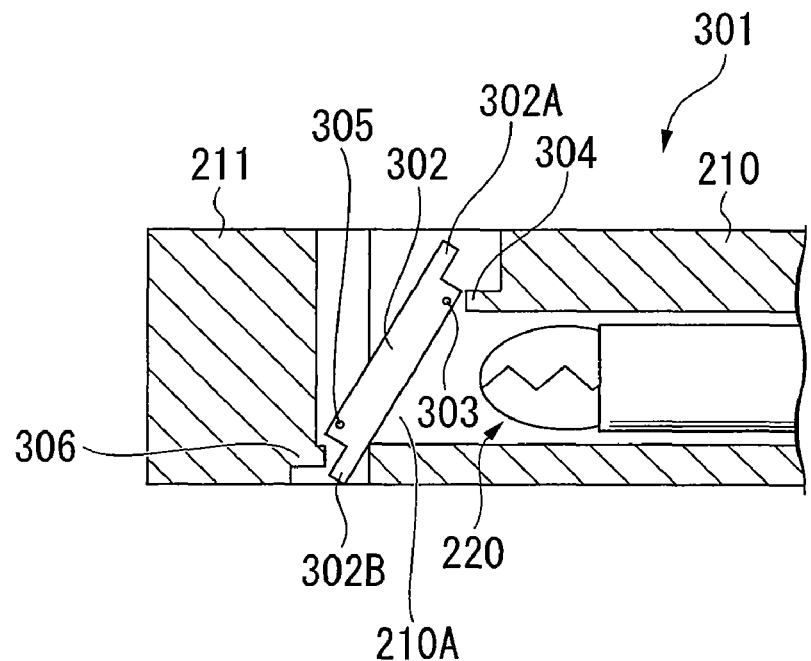
FIG. 27 is a sectional view showing the tip portion having a configuration in which the image pickup device is offset using a link.
Figure 28:
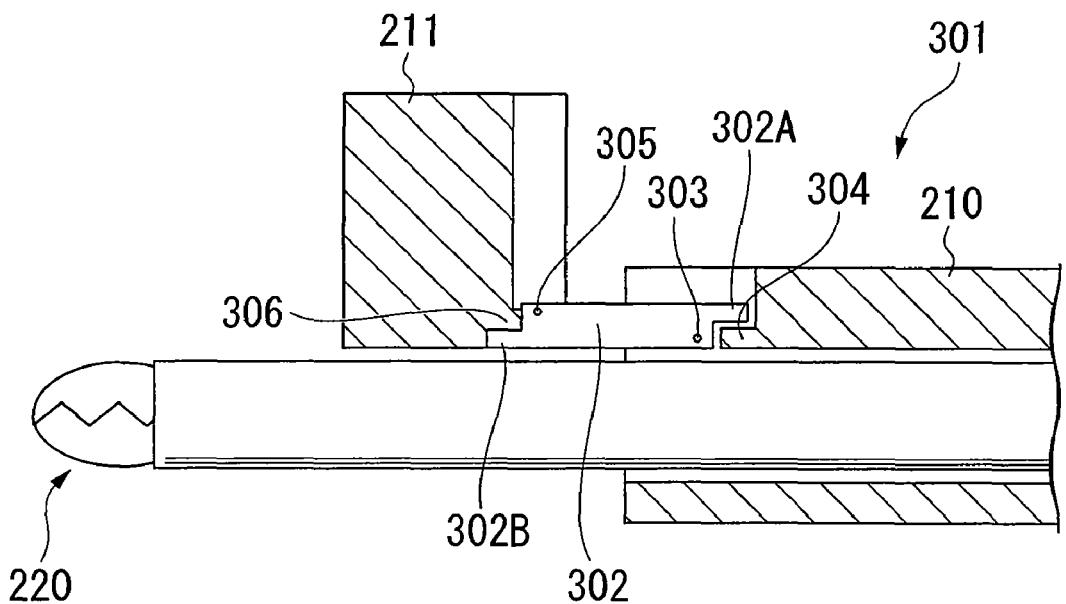
FIG. 28 is a view showing a state in which the pivotable forceps being in the state shown in FIG. 27 are protruded to push up and offset the image pickup device.

FIG. 27 and FIG. 28 show a modification example of the surgical treatment apparatus. In the surgical treatment apparatus 301 shown in the figures, the image pickup device 211 is disposed at the tip portion of the outer sheath 210 so as to be concentric therewith via a link member 302. The link member 302 is freely rotatably supported on the outer sheath 210 via a pin 303 and has a stopper 302A that is protruded and can be engaged with a step 304 formed on the outer sheath 210. On the side of the image pickup device 211, the link member 302 is freely rotatably supported via a pin 305 and has a stopper 302B that is protruded and can be engaged with a step 306 formed on the image pickup device 211. The forceps 240 are passed through the pivotable forceps 220 so as to freely extend/retract.

When the apparatus is inserted into the body, the image pickup device 211 is disposed concentrically with the outer sheath 210. When treatment is carried out, the pivotable forceps 220 are extended. The pair of forceps members 37 press the image pickup device 211 and rotate the link member 302. The image pickup device 211 is thus moved to a position offset from the axis line. The stoppers 302A and 302B make contact with the steps 304 and 306, respectively, and the amount of the rotation is restricted. Hence, the image pickup device 211 can take images of the working area of the pivotable forceps 220. When the pivotable forceps 220 are retracted into the outer sheath 210, the link member 302 is rotated, and the image pickup device 211 is returned to its original position on the axis line of the outer sheath 210. Since the position of the image pickup device 211 can be changed by pushing/pulling the pivotable forceps 220, the operation is made easy. It is thus not necessary to install a device for changing the position of the image pickup device 211 on the elements handled by the operator. Hence, the configuration of the apparatus is simplified.

Figure 29:
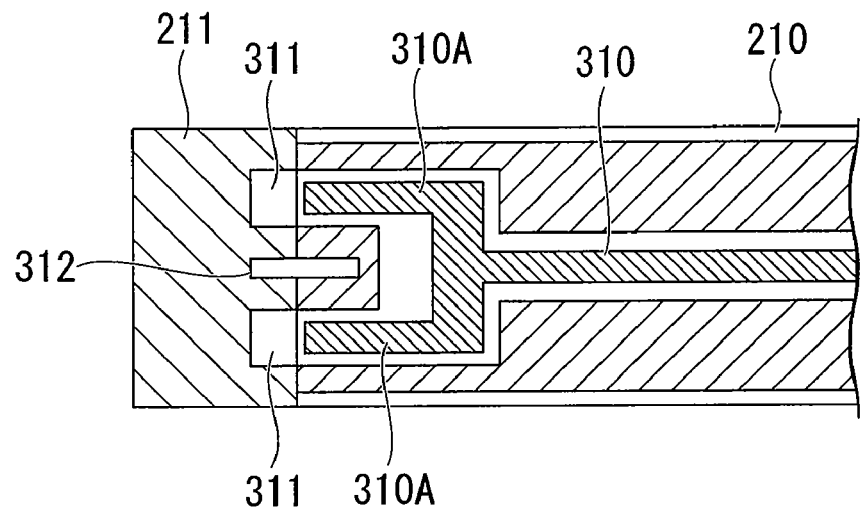
FIG. 29 is an enlarged view showing the tip portion having a mechanism for locking the rotation of the image pickup device.
Figure 30:
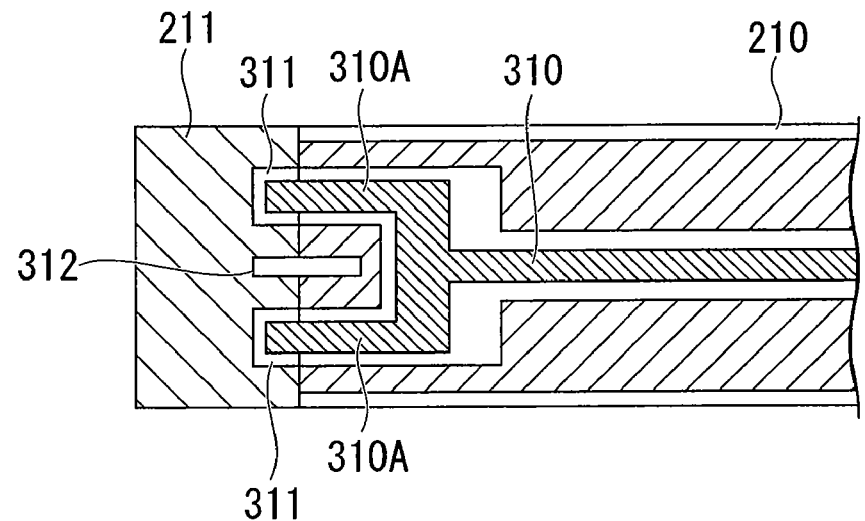
FIG. 30 is a view showing a state in which the image pickup device is locked so as not to be rotatable.

As shown in FIG. 29 and FIG. 30, a rotation preventing member 310 may also be provided in the outer sheath 210. The rotation preventing member 310 has a pin 310A that can be protruded from and sunk into the tip portion of the outer sheath 210 subject to the manipulation of operator. In the image pickup device 211, a hole 311 is formed into which the pin 310A can be inserted when the image pickup device 211 is moved to its offset position. When the pin 310A is pushed into the hole, the image pickup device 211 having moved to its offset position cannot return to its original position. FIG. 29 and FIG. 30 show an example in which the rotation preventing member 310 is provided in a configuration in which the image pickup device 211 is rotatable via a pin 312. However, the rotation preventing member 310 may also be provided in a configuration in which the rotation rod 212 or the link member 302 is used.

Although the present invention has been described with respect to its preferred embodiments, the present invention is not limited to the embodiments described above. The configuration of the present invention allows for addition, omission, substitution and further replacement without departing from the spirit and scope of the present invention. The present invention is not limited by the above descriptions but is limited only by the appended claims.

What is claimed is:

1. A surgical treatment apparatus comprising:
   an outer sheath, extending from a base portion subject to an operator's hand to the tip subject to insertion into a body cavity, that is provided with a working channel through which a treatment instrument can be passed;
   an image pickup device disposed at a tip portion of the outer sheath and being movable to a position offset from a central axis line of the outer sheath;
   pivotable forceps passed through the outer sheath so as to freely extend/retract and provided with a pair of forceps members arranged so as to be freely opened/closed and freely bent in a direction substantially orthogonal to the opening/closing direction thereof, the pivotable forceps provided with a hollow sheath; and
   a second forceps instrument inserted into the hollow sheath so as to freely extend/retract, and arranged so as to be freely protruded from and sunk into an opening formed in the hollow sheath of the pivotable forceps and used to treat tissue inside the body when the forceps members are bent.

2. The surgical treatment apparatus according to claim 1, wherein
   the image pickup device is secured to a rotation rod passed through the outer sheath, the rotation rod is passed through at a position offset from the axis line of the outer sheath, and an operation section for rotating the rotation rod is provided on the hand side of the operator.

3. The surgical treatment apparatus according to claim 1, wherein
   the pivotable forceps are rotatable with respect to the outer sheath and the treatment instrument.

* * * * *